(12) United States Patent
Kang

(10) Patent No.: US 7,238,851 B2
(45) Date of Patent: Jul. 3, 2007

(54) NON-HUMAN TRANSGENIC MAMMALS EXPRESSING AN N-3 DESATURASE GENE

(75) Inventor: Jing X. Kang, North Andover, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/468,318

(22) PCT Filed: Mar. 12, 2002

(86) PCT No.: PCT/US02/07649

§ 371 (c)(1),
(2), (4) Date: Jan. 12, 2004

(87) PCT Pub. No.: WO02/072028

PCT Pub. Date: Sep. 19, 2002

(65) Prior Publication Data

US 2004/0115681 A1 Jun. 17, 2004

Related U.S. Application Data

(60) Provisional application No. 60/275,222, filed on Mar. 12, 2001.

(51) Int. Cl.
*C12N 15/00* (2006.01)
(52) U.S. Cl. .................. 800/14; 800/14; 800/15; 800/16; 800/17; 800/18
(58) Field of Classification Search .............. 800/8, 800/14–18; 435/455; 536/23.1
See application file for complete search history.

(56) References Cited

U.S. PATENT DOCUMENTS

2003/0196217 A1* 10/2003 Mukerji et al. ............. 800/281

OTHER PUBLICATIONS

Spychalla PNAS, USA, 94: 1142-1147 (Feb. 1997).*
Strunk et al. (2004) Phenotypic variation resulting from a deficiency of epidermal growth factor receptor in mice is caused by extensive genetic heterogeneity that can be genetically and molecularly partitioned. Gentics 167:1821-1832.*
Sanford et al. (2001) Influence of Genetic Background on knockout mouse phenotypes. Methods Mol. Biol. 158:217-225.*
Cameron et al. (1997) Recent Advances in Transgenic Technology. Molecular Biotechnology. 7:253-265.*
Wall et al. (1996) Transgenic Livestock: Progress and prospects for the future. Theriogenology 45:57-68.*
Houdebine et al. (1994) Production of pharmaceutical proteins from transgenic animals. Journal of Biotechnology. 34:269-287.*
Sequence alignment (Mar. 29, 2005) pp. 1-7.*
Sigmund, C., Jun. 2000, Arterioscler. Thromb. Vasc. Biol., p. 1425-1429.*
Houdebine, L-M., 2002, Journal of Biotechnology, vol. 98, p. 145-160.*
Kolb et al. (1999) Insertion of a foriegn gene into the beta-casein locus by Cre-mediated site-specific recombination. Gene 227:21-31.*
Houdebine. (2000) Transgenic animal bioreactors. Transgenic Research. 9:305-320.*
Murray et al. (1999) Genetic modification of animals in the next century. Theriogenoogy. 51:149-159.*
Albert et al., *JAMA* 279:23-28 (1998).
Agren et al., *Prostagland. Leukot. Essent. Fatty Acids* 57:419-421 (1997).
AHA Dietary Guidelines: Revision 2000, Circulation 102:2284-2299 (2000).
Appel et al., *Arch. Intern. Med.* 153:1429-1438 (1993).
Ariza-Ariza et al., *Semin. Arthritis Rheum.* 27:366-370 (1998).
Arondel et al., *Science* 258:1353-1355 (1992).
Belluzzi et al., *N. Engl. J. Med.* 334:1557-1560 (1996).
Bezzi et al., *Nature* 391:281-285 (1998).
Bougnoux, *Curr. Opin. Clin. Nutr. Metab. Care* 2:121-126 (1999).
Broun et al., *Annu. Rev. Nutr.* 19:197-216 (1999).
Browse and Somerville, *Annu. Rev. Plant Physiol. Plant Mol. Biol.* 42:467-506 (1991).
Calder, *Ann. Nutr. Metab.* 41:203-234 (1997).
Carrie et al., *Neurosci. Lett.* 266:69-72 (1999).
Cave, *Breast Cancer Res. Treat.* 46:239-246 (1997).
Clandinin et al., *Can. J. Physiol. Pharmacol.* 63:546-556 (1985).
Clarke, *Br. J. Nutr.* 83:S59-S66 (2000).
Connor, *Am. J. Clin. Nutr.* 70:951-952 (1999).
Diaz et al., *J. Virol.* 72:789-795 (1998).
De Caterina et al., *Kidney Int.* 44:843-850 (1993).
DeLorgeril et al., *Circulation* 99:779-785 (1999).
Drachman and Rothstein, *Ann Neurol.* 48:792-795 (2000).
Dyerberg and Bang, *Lancet* 2:433-435 (1979).
Dyerberg et al., *Lancet* 2:117-119 (1978).

(Continued)

*Primary Examiner*—Deborah Crouch
(74) *Attorney, Agent, or Firm*—Edwards Angell Palmer & Dodge LLP; Peter C. Lauro, Esq.; Marina I. Heusch

(57) ABSTRACT

The present invention features compositions (e.g, nucleic acids encoding fat-1, optionally and operably linked to a constitutively active or tissue-specific promoter or other regulatory sequence and pharmaceutically acceptable formulations including that nucleic acid or biologically active variants thereof) and methods that can be used to effectively modify the content of PUFAs in animal cells (i.e., cells other than those of *C. elegants*, for example, mammalian cells such as myocytes, neurons (whether of the periferal or central nervous system), adipocytes, endothelial cells, and cancer cells). The modified cells, whether in vivo or ex vivo (e.g., in tissue culture), transgenic animals containing them, and food products obtained from those animals (e.g., meat or other edible parts of the animals (e.g., liver, kidney, or sweetbreads)) are also within the scope of the present invention.

16 Claims, 18 Drawing Sheets

OTHER PUBLICATIONS

Gill and Valivety, *Trends Biotechnol.* 15:401-409 (1997).
GISSI-Prevenzione Investigators, *Lancet* 354:447-455 (1999).
Goodnight et al., *Blood* 58:880-885 (1981).
Guallar et al., *Arterioscler. Thromb. Vasc. Biol.* 19:1111-1118 (1999).
Hajjar et al., *Circulation* 95:423-429 (1997).
Hajjar et al., *Circ. Res.* 81:145-153 (1997).
Hajjar et al., *Proc. Natl. Acad. Sci. USA* 95:5251-5256 (1998).
Harris, *Am. J. Clin. Nutr.* 65:1645S-1654S (1997).
He et al., *Proc. Natl. Acad. Sci. USA* 95:2509-2514 (1998).
Ho et al., *Cancer Res.* 53:641-651 (1993).
Hoffman and Birch, *World Rev. Nutr. Diet* 83:52-60 (1998).
Hu et al., *Cancer Res.* 57(16):3339-3343 (1997).
Hu et al., *Am. J. Clin. Nutr.* 69:890-897 (1999).
James et al., *Am. J. Clin Nutr.* 71:343S-348S (2000).
Kang and Leaf, *Circulation* 94:1774-1780 (1996).
Kang et al., *Biochim. Biophys. Acta* 1128:267-274 (1992).
Kang et al., *Proc. Natl. Acad. Sci. USA* 98:4050-4054 (2001).
Kaneko et al., *Cancer Res.* 55:5283-5287 (1995).
Knutzon et al., *J. Biol. Chem.* 273:29360-29366 (1998).
Kremer, *Am. J. Clin. Nutr.* 71:349S-351S (2000).
Leaf and Kang, *World Rev. Nutr. Diet.* 83:24-37 (1998).
Leaf and Weber, *Am. J. Clin. Nutr.* 45:1048-1053 (1987).
Mahendroo et al., *J. Biol. Chem.* 268:19463-19470 (1993).
McLennan et al., *Am. Heart J.* 116:709-717 (1988).
Miyatake et al., *J. Virol.* 71:5124-5132 (1997).
Mori et al., *Arterioscler. Throm. Vasc. Biol.* 17:279-286 (1997).
Napier et al., *Curr. Opin. Plant Biol.* 2:123-127 (1999).
Needleman et al., *Ann. Rev. Biochem.* 55:69-102 (1986).
Neuringer et al., *Proc. Natl. Acad. Sci USA* 83:4021-4025 (1986).
Niwa et al., *Gene* 108:193-200 (1991).
Okabe et al., *FEBS Lett.* 407:313-319 (1997).
O'Keefe and Harris, *Mayo Clin. Proc.* 75:607-614 (2000).
Okuley et al., *Plant Cell* 6:147-158 (1994).
Otto et al., *Transplantation* 50:193-198 (1990).
Ozaki et al., *Hum Gene Ther.* 7:1483-1490 (1996).
Price et al., *Curr. Opin. Lipidol.* 11:3-7 (2000).
Raheja et al., *Ann. N.Y. Acad. Sci.* 683:258-271 (1993).
Reddy et al., *Trends Neurosc.* 22:248-255 (1999).
Rose and Connolly, *Pharmacol. Ther.* 83:217-244 (1999).
Ruther et al., *EMBO J.*, 2:1794 (1983).
Salem et al., *Lipids* 31:S1-S326 (1996).
Sanzgiri et al., *J. Neurobiol.* 41:221-229 (1999).
Schousboe et al., In a Dissection and Tissue Culture Manual of the Nervous System, Shahar et al., Eds., Alan R. Liss, New York, N.Y., pp. 203-206 (1989).
Sellmayer et al., *Lipids* 31:S37-S40 (1996).
Shahar et al., *N. Engl. J. Med.* 331:228-233 (1994).
Shi et al., *Hum Gene Ther.* 8:403-410 (1997).
Simpson et al., *Clin. Chem.* 39:317-324 (1993).
Simopoulos, *Am. J. Clin. Nutr.* 70:560S-569S (1999).
Simopoulos, *Food Australia* 51:332-333 (1999).
Simopoulos, *Poultry Science* 79:961-970 (2000).
Singh et al., *Cardiovasc. Drugs Ther.* 11:485-491 (1997).
Siscovick et al., *JAMA* 274:1363-1367 (1995).
Smith and Borgeat, In Biochemistry of Lipids and Membranes, D.E. Vance, Eds., Benjamin/Cummings, Menlo Park, CA, 00 325-360 (1985).
Smith and Johnson, *Gene* 67:31-40 (1988).
Spychalla et al., *Proc. Natl. Acad. Sci. USA* 94:1142-1147 (1997).
Stenson et al., *Ann. Intern. Med.* 116:609-614 (1992).
Suzuki et al., *Hum Gene Ther.* 7:1883-1893 (1996).
Uauy et al., *Proc. Nutr. Soc.* 59:3-15 (2000).
Uauy et al., *Lipids* 36:885-895 (2001).
Vancassel et al., *Prost. Leuk. Ess. Fatt. Acids* 65:1-7 (2001).
Von Schacky et al., *Ann. Intern. Med.* 130:554-562 (1999).
Von Schacky, *J. Lab. Clin. Med.* 128:5-6 (1996).
Wada et al., *Nucleic Acids Res.* 20:2111-2118 (1992).
Weylandt et al., *Lipids* 31:977-982 (1996).
Ziboh, *World Rev. Nutr. Diet* 66:425-435 (1991).
Kelder et al. "Expression of fungal desaturase in cultured mammalian cells." Molecular and Cellular Biochemistry 219: 7-11 (2001).
Yadav et al. "Cloning of Higher Plant w-3 Fatty Acid Desaturases." Plant Physiol. 103: 467-476 (1993).
Sakamoto et al. "Cloning of w3 desaturase from cyanobacteria and its use in altering the degree of membrane-lipid unsaturation." Plant Molecular Biology 26: 249-263 (1994).

* cited by examiner

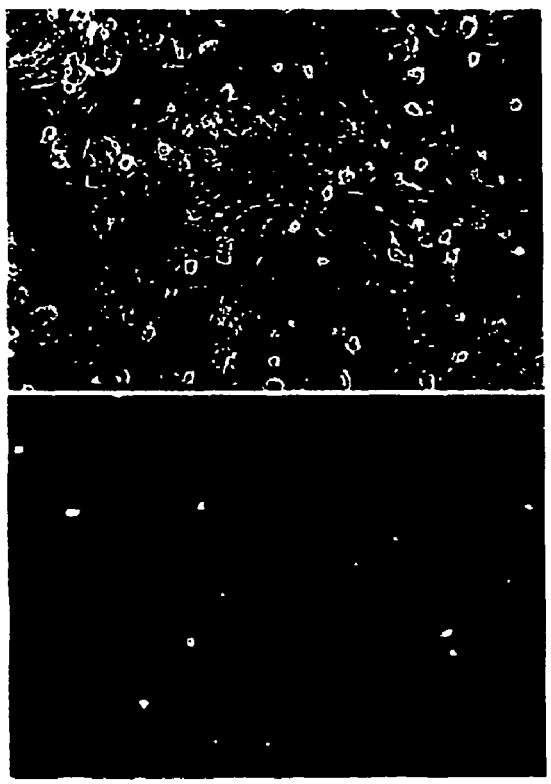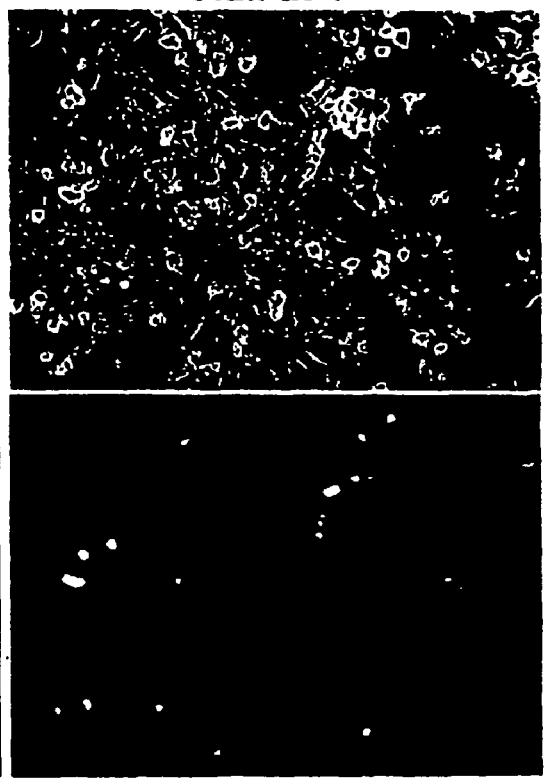
Fig. 1

| Mol % of total Fatty acids | Control | Fat-1 |
|---|---|---|
| n-6 Polyunsaturates | | |
| 18:2n-6 | 14.2[a] | 9.2[b] |
| 20:2n-6 | 1.2[a] | 0.3[b] |
| 20:3n-6 | 1.6[a] | 0.4[b] |
| 20:4n-6 | 15.2[a] | 4.1[b] |
| 22:4n-6 | 4.4[a] | 1.0[b] |
| 22:5n-6 | 0.2[a] | 0.0[b] |
| Total | 36.8[a] | 15.0[b] |
| n-3 Polyunsaturates | | |
| 18:3n-3 | 0.2[b] | 3.6[a] |
| 20:4n-3 | 0.0[b] | 0.6[a] |
| 20:5n-3 | 0.1[b] | 6.1[a] |
| 22:5n-3 | 1.2[b] | 5.8[a] |
| 22:6n-3 | 1.0[a] | 1.3[a] |
| Total | 2.5[b] | 17.4[a] |
| n-6/n-3 Ratio | 14.7[a] | 0.9[b] |

Values are means of four measurements. Values for each fatty acid with the same letter do not differ significantly ($P<0.01$) between control and fat-1.

Fig. 5

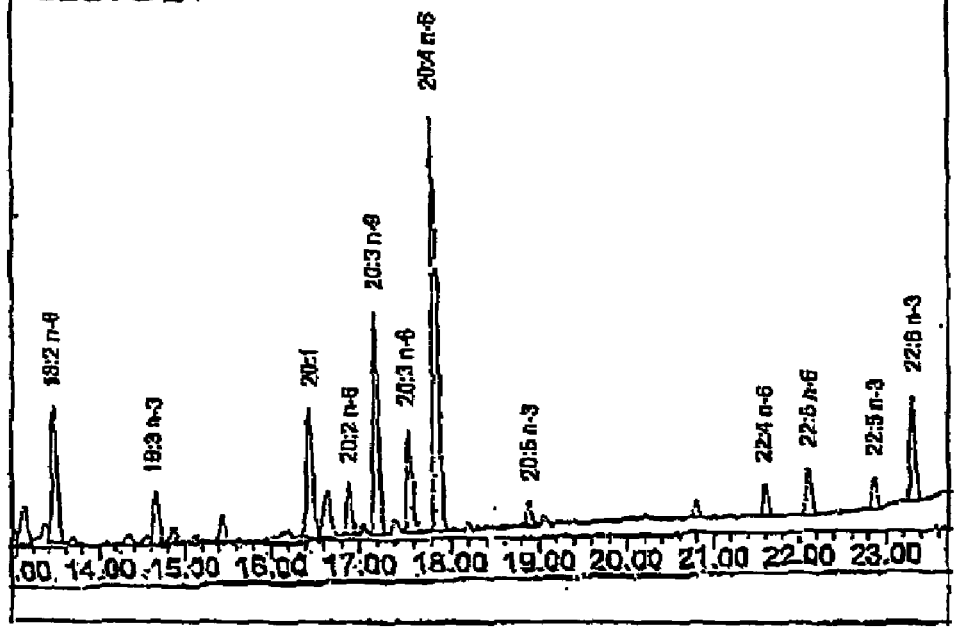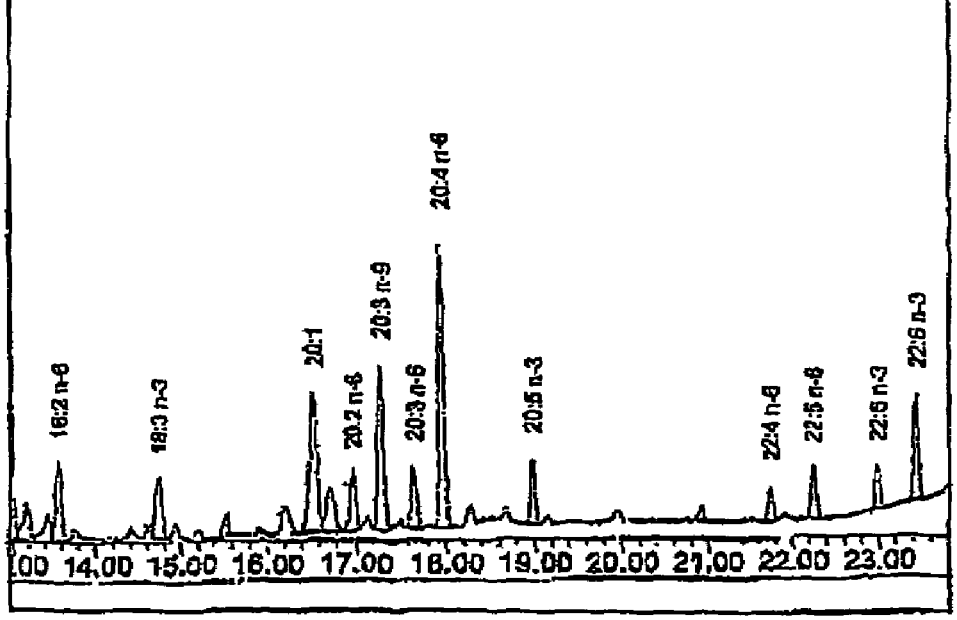
Fig. 9

PUFA composition of total cellular lipids from the control rat cortical and the transgenic cells expressing a *C. elegans fat-1* cDNA

| Mol % of total fatty acids | Control | *fat-1* |
|---|---|---|
| n-6 Polyunsaturates | | |
| 18:2n-6 | 1.78 | 0.87 |
| 20:4n-6 | 7.21 | 4.23 |
| 22:4n-6 | 1.57 | 0.72 |
| 22:5n-6 | 1.68 | 0.72 |
| Total | 12.26 | 6.53 |
| n-3 Polyunsaturates | | |
| 18:3n-3 | 0.34 | 0.86 |
| 20:5n-3 | 0.21 | 0.87 |
| 22:5n-3 | 0.29 | 0.81 |
| 22:6n-3 | 1.27 | 1.93 |
| Total | 2.11 | 4.48 |
| n-6/n-3 Ratio | 6.44 | 1.67 |

Values are means of four measurements. ($p<0.01$) between control and fat-1.

Fig. 10

Ad.GFP
↑Ca⁺⁺ (7.5mM)
Ad.GFP.Fat-1
↑Ca⁺⁺ (7.5mM)
Fig. 13

PUFA composition of total cellular lipids from the control MCF-7 and the transgenic cells expressing a *C. elegans fat-1* cDNA

| Mol % of total fatty acids | Control | Fat-1 |
|---|---|---|
| n-6 Polyunsaturates | | |
| 18:2n-6 | 3.13[a] | 1.51[b] |
| 20:2n-6 | 0.23[a] | 0.22[a] |
| 20:3n-6 | 0.34[a] | 0.16[b] |
| 20:4n-6 | 6.30[a] | 2.26[b] |
| 22:4n-6 | 0.53[a] | 0.33[b] |
| 22:5n-6 | 0.27[a] | 0.11[b] |
| Total | 10.80[a] | 4.59[b] |
| n-3 Polyunsaturates | | |
| 18:3n-3 | 0.0[b] | 1.00[a] |
| 20:4n-3 | 0.0[b] | 0.10[a] |
| 20:5n-3 | 0.0[b] | 2.87[a] |
| 22:5n-3 | 0.33[b] | 1.47[a] |
| 22:6n-3 | 0.60[a] | 0.73[a] |
| Total | 0.93[b] | 6.17[b] |
| n-6/n-3 Ratio | 11.61[a] | 0.74[b] |

Values are means of four measurements. Values for each fatty acid with the same letter do not differ significantly ($p<0.01$) between control and fat-1.

Fig. 15

```
CAAGTTTGAG GT                                                                    12

ATG GTC GCT CAT TCC TCA GAA GGG TTA TCC GCC ACG GCT CCG GTC      57
Met Val Ala His Ser Ser Glu Gly Leu Ser Ala Thr Ala Pro Val
             5               10              15

ACC GGC GGA GAT GTT CTG GTT GAT GCT CGT GCA TCT CTT GAA GAA      102
Thr Gly Gly Asp Val Leu Val Asp Ala Arg Ala Ser Leu Glu Glu
             20              25              30

AAG GAG GCT CCA CGT GAT GTG AAT GCA AAC ACT AAA CAG GCC ACC      147
Lys Glu Ala Pro Arg Asp Val Asn Ala Asn Thr Lys Gln Ala Thr
             35              40              45

ACT GAA GAG CCA CGC ATC CAA TTA CCA ACT GTG GAT GCT TTC CGT      192
Thr Glu Glu Pro Arg Ile Gln Leu Pro Thr Val Asp Ala Phe Arg
             50              55              60

CGT GCA ATT CCA GCA CAC TGT TTC GAA AGA GAT CTC GTT AAA TCA      237
Arg Ala Ile Pro Ala His Cys Phe Glu Arg Asp Leu Val Lys Ser
             65              70              75

ATC AGA TAT TTG GTG CAA GAC TTT GCG GCA CTC ACA ATT CTC TAC      282
Ile Arg Tyr Leu Val Gln Asp Phe Ala Ala Leu Thr Ile Leu Tyr
             80              85              90

TTT GCT CTT CCA GCT TTT GAG TAC TTT GGA TTG TTT GGT TAC TTG      327
Phe Ala Leu Pro Ala Phe Glu Tyr Phe Gly Leu Phe Gly Tyr Leu
             95              100             105

GTT TGG AAC ATT TTT ATG GGA GTT TTT GGA TTC GCG TTG TTC GTC      372
Val Trp Asn Ile Phe Met Gly Val Phe Gly Phe Ala Leu Phe Val
             110             115             120

GTT GGA CAC GAT TGT CTT CAT GGA TCA TTC TCT GAT AAT CAG AAT      417
Val Gly His Asp Cys Leu His Gly Ser Phe Ser Asp Asn Gln Asn
             125             130             135

CTC AAT GAT TTC ATT GGA CAT ATC GCC TTC TCA CCA CTC TTC TCT      462
Leu Asn Asp Phe Ile Gly His Ile Ala Phe Ser Pro Leu Phe Ser
             140             145             150

CCA TAC TTC CCA TGG CAG AAA AGT CAC AAG CTT CAC CAT GCT TTC      507
Pro Tyr Phe Pro Trp Gln Lys Ser His Lys Leu His His Ala Phe
             155             160             165

ACC AAC CAC ATT GAC AAA GAT CAT GGA CAC GTG TGG ATT CAG GAT      552
Thr Asn His Ile Asp Lys Asp His Gly His Val Trp Ile Gln Asp
             170             175             180

AAG GAT TGG GAA GCA ATG CCA TCA TGG AAA AGA TGG TTC AAT CCA      597
Lys Asp Trp Glu Ala Met Pro Ser Trp Lys Arg Trp Phe Asn Pro
             185             190             195

ATT CCA TTC TCT GGA TGG CTT AAA TGG TTC CCA GTG TAC ACT TTA      642
Ile Pro Phe Ser Gly Trp Leu Lys Trp Phe Pro Val Tyr Thr Leu
             200             205             210

TTC GGT TTC TGT GAT GGA TCT CAC TTC TGG CCA TAC TCT TCA CTT      687
```

Fig. 17A

```
Phe Gly Phe Cys Asp Gly Ser His Phe Trp Pro Tyr Ser Ser Leu
              215                  220                  225

TTT GTT CGT AAC TCT GAC CGT GTT CAA TGT GTA ATC TCT GGA ATC      732
Phe Val Arg Asn Ser Asp Arg Val Gln Cys Val Ile Ser Gly Ile
              230                  235                  240

TGT TGC TGT GTG TGT GCA TAT ATT GCT CTA ACA ATT GCT GGA TCA      777
Cys Cys Cys Val Cys Ala Tyr Ile Ala Leu Thr Ile Ala Gly Ser
              245                  250                  255

TAT TCC AAT TGG TTC TGG TAC TAT TGG GTT CCA CTT TCT TTC TTC      822
Tyr Ser Asn Trp Phe Trp Tyr Tyr Trp Val Pro Leu Ser Phe Phe
              260                  265                  270

GGA TTG ATG CTC GTC ATT GTT ACC TAT TTG CAA CAT GTC GAT GAT      867
Gly Leu Met Leu Val Ile Val Thr Tyr Leu Gln His Val Asp Asp
              275                  280                  285

GTC GCT GAG GTG TAC GAG GCT GAT GAA TGG AGC TTC GTC CGT GGA      912
Val Ala Glu Val Tyr Glu Ala Asp Glu Trp Ser Phe Val Arg Gly
              290                  295                  300

CAA ACC CAA ACC ATC GAT CGT TAC TAT GGA CTC GGA TTG GAC ACA      957
Gln Thr Gln Thr Ile Asp Arg Tyr Tyr Gly Leu Gly Leu Asp Thr
              305                  310                  315

ACG ATG CAC CAT ATC ACA GAC GGA CAC GTT GCC CAT CAC TTC TTC     1002
Thr Met His His Ile Thr Asp Gly His Val Ala His His Phe Phe
              320                  325                  330

AAC AAA ATC CCA CAT TAC CAT CTC ATC GAA GCA ACC GAA GGT GTC     1047
Asn Lys Ile Pro His Tyr His Leu Ile Glu Ala Thr Glu Gly Val
              335                  340                  345

AAA AAG GTC TTG GAG CCG TTG TCC GAC ACC CAA TAC GGG TAC AAA     1092
Lys Lys Val Leu Glu Pro Leu Ser Asp Thr Gln Tyr Gly Tyr Lys
              350                  355                  360

TCT CAA GTG AAC TAC GAT TTC TTT GCC CGT TTC CTG TGG TTC AAC     1137
Ser Gln Val Asn Tyr Asp Phe Phe Ala Arg Phe Leu Trp Phe Asn
              365                  370                  375

TAC AAG CTC GAC TAT CTC GTT CAC AAG ACC GCC GGA ATC ATG CAA     1182
Tyr Lys Leu Asp Tyr Leu Val His Lys Thr Ala Gly Ile Met Gln
              380                  385                  390

TTC CGA ACA ACT CTC GAG GAG AAG GCA AAG GCC AAG TAA             1221
Phe Arg Thr Thr Leu Glu Glu Lys Ala Lys Ala Lys
              395                  400

AAGAATATCC CGTGCCGTTC TAGAGTACAA CAACAACTTC TGCGTTTTCA           1271

CCGGTTTTGC TCTAATTGCA ATTTTTCTTT GTTCTATATA TATTTTTTG            1321

CTTTTTAATT TTATTCTCTC TAAAAAACTT CTACTTTCA GTGCGTTGAA            1371

TGCATAAAGC CATAACTCTT                                            1391
```

Fig. 17B

SEQUENCE LISTING

<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Synthetically generated primer

<400> SEQUENCE: 1
agaattcggc acgagccaag tttgaggt                                    28

<210> SEQ ID NO 2
<211> LENGTH: 28
<212> TYPE: DNA
<213> ORGANISM: Artificial Sequence
<220> FEATURE:
<223> OTHER INFORMATION: Synthetically generated primer

<400> SEQUENCE: 2
gcctgaggct ttatgcattc aacgcact                                    28

<210> SEQ ID NO 3
<211> LENGTH: 1391
<212> TYPE: DNA
<213> ORGANISM: Caenorhabditis elegans
<220> FEATURE:
<221> NAME/KEY: CDS
<222> LOCATION: (13)...(1221)

<400> SEQUENCE: 3

```
caagtttgag gt atg gtc gct cat tcc tca gaa ggg tta tcc gcc acg gct      51
              Met Val Ala His Ser Ser Glu Gly Leu Ser Ala Thr Ala
                1               5                  10 ccg gtc acc ggc gga gat gtt ctg gtt gat gct cgt gca tct ctt gaa        99
Pro Val Thr Gly Gly Asp Val Leu Val Asp Ala Arg Ala Ser Leu Glu
        15                  20                  25 gaa aag gag gct cca cgt gat gtg aat gca aac act aaa cag gcc acc       147
Glu Lys Glu Ala Pro Arg Asp Val Asn Ala Asn Thr Lys Gln Ala Thr
 30              35                  40                  45 act gaa gag cca cgc atc caa tta cca act gtg gat gct ttc cgt cgt       195
Thr Glu Glu Pro Arg Ile Gln Leu Pro Thr Val Asp Ala Phe Arg Arg
                    50                  55                  60 gca att cca gca cac tgt ttc gaa aga gat ctc gtt aaa tca atc aga       243
Ala Ile Pro Ala His Cys Phe Glu Arg Asp Leu Val Lys Ser Ile Arg
                65                  70                  75 tat ttg gtg caa gac ttt gcg gca ctc aca att ctc tac ttt gct ctt       291
Tyr Leu Val Gln Asp Phe Ala Ala Leu Thr Ile Leu Tyr Phe Ala Leu
            80                  85                  90 cca gct ttt gag tac ttt gga ttg ttt ggt tac ttg gtt tgg aac att       339
Pro Ala Phe Glu Tyr Phe Gly Leu Phe Gly Tyr Leu Val Trp Asn Ile
        95                  100                 105 ttt atg gga gtt ttt gga ttc gcg ttg ttc gtc gtt gga cac gat tgt       387
Phe Met Gly Val Phe Gly Phe Ala Leu Phe Val Val Gly His Asp Cys
110                 115                 120                 125
```

| | |
|---|---|
| ctt cat gga tca ttc tct gat aat cag aat ctc aat gat ttc att gga<br>Leu His Gly Ser Phe Ser Asp Asn Gln Asn Leu Asn Asp Phe Ile Gly<br>130 135 140 | 435 |
| cat atc gcc ttc tca cca ctc ttc tct cca tac ttc cca tgg cag aaa<br>His Ile Ala Phe Ser Pro Leu Phe Ser Pro Tyr Phe Pro Trp Gln Lys<br>145 150 155 | 483 |
| agt cac aag ctt cac cat gct ttc acc aac cac att gac aaa gat cat<br>Ser His Lys Leu His His Ala Phe Thr Asn His Ile Asp Lys Asp His<br>160 165 170 | 531 |
| gga cac gtg tgg att cag gat aag gat tgg gaa gca atg cca tca tgg<br>Gly His Val Trp Ile Gln Asp Lys Asp Trp Glu Ala Met Pro Ser Trp<br>175 180 185 | 579 |
| aaa aga tgg ttc aat cca att cca ttc tct gga tgg ctt aaa tgg ttc<br>Lys Arg Trp Phe Asn Pro Ile Pro Phe Ser Gly Trp Leu Lys Trp Phe<br>190 195 200 205 | 627 |
| cca gtg tac act tta ttc ggt ttc tgt gat gga tct cac ttc tgg cca<br>Pro Val Tyr Thr Leu Phe Gly Phe Cys Asp Gly Ser His Phe Trp Pro<br>210 215 220 | 675 |
| tac tct tca ctt ttt gtt cgt aac tct gac cgt gtt caa tgt gta atc<br>Tyr Ser Ser Leu Phe Val Arg Asn Ser Asp Arg Val Gln Cys Val Ile<br>225 230 235 | 723 |
| tct gga atc tgt tgc tgt gtt tgt gca tat att gct cta aca att gct<br>Ser Gly Ile Cys Cys Cys Val Cys Ala Tyr Ile Ala Leu Thr Ile Ala<br>240 245 250 | 771 |
| gga tca tat tcc aat tgg ttc tgg tac tat tgg gtt cca ctt tct ttc<br>Gly Ser Tyr Ser Asn Trp Phe Trp Tyr Tyr Trp Val Pro Leu Ser Phe<br>255 260 265 | 819 |
| ttc gga ttg atg ctc gtc att gtt acc tat ttg caa cat gtc gat gat<br>Phe Gly Leu Met Leu Val Ile Val Thr Tyr Leu Gln His Val Asp Asp<br>270 275 280 285 | 867 |
| gtc gct gag gtg tac gag gct gat gaa tgg agc ttc gtc cgt gga caa<br>Val Ala Glu Val Tyr Glu Ala Asp Glu Trp Ser Phe Val Arg Gly Gln<br>290 295 300 | 915 |
| acc caa acc atc gat cgt tac tat gga ctc gga ttg gac aca acg atg<br>Thr Gln Thr Ile Asp Arg Tyr Tyr Gly Leu Gly Leu Asp Thr Thr Met<br>305 310 315 | 963 |
| cac cat atc aca gac gga cac gtt gcc cat cac ttc ttc aac aaa atc<br>His His Ile Thr Asp Gly His Val Ala His His Phe Phe Asn Lys Ile<br>320 325 330 | 1011 |
| cca cat tac cat ctc atc gaa gca acc gaa ggt gtc aaa aag gtc ttg<br>Pro His Tyr His Leu Ile Glu Ala Thr Glu Gly Val Lys Lys Val Leu<br>335 340 345 | 1059 |
| gag ccg ttg tcc gac acc caa tac ggg tac aaa tct caa gtg aac tac<br>Glu Pro Leu Ser Asp Thr Gln Tyr Gly Tyr Lys Ser Gln Val Asn Tyr<br>350 355 360 365 | 1107 |
| gat ttc ttt gcc cgt ttc ctg tgg ttc aac tac aag ctc gac tat ctc<br>Asp Phe Phe Ala Arg Phe Leu Trp Phe Asn Tyr Lys Leu Asp Tyr Leu<br>370 375 380 | 1155 |
| gtt cac aag acc gcc gga atc atg caa ttc cga aca act ctc gag gag<br>Val His Lys Thr Ala Gly Ile Met Gln Phe Arg Thr Thr Leu Glu Glu<br>385 390 395 | 1203 |
| aag gca aag gcc aag taa aagaatatcc cgtgccgttc tagagtacaa<br>Lys Ala Lys Ala Lys *<br>400 | 1251 |
| caacaacttc tgcgttttca ccggtttgc tctaattgca atttttcttt gttctatata | 1311 |
| tattttttg cttttaatt ttattctctc taaaaaactt ctactttca gtgcgttgaa | 1371 |
| tgcataaagc cataactctt | 1391 |

<210> SEQ ID NO 4
<211> LENGTH: 402
<212> TYPE: PRT
<213> ORGANISM: Caenorhabditis elegans

<400> SEQUENCE: 4

Met Val Ala His Ser Ser Glu Gly Leu Ser Ala Thr Ala Pro Val Thr
1               5                   10                  15

Gly Gly Asp Val Leu Val Asp Ala Arg Ala Ser Leu Glu Glu Lys Glu
            20                  25                  30

Ala Pro Arg Asp Val Asn Ala Asn Thr Lys Gln Ala Thr Thr Glu Glu
        35                  40                  45

Pro Arg Ile Gln Leu Pro Thr Val Asp Ala Phe Arg Arg Ala Ile Pro
50                  55                  60

Ala His Cys Phe Glu Arg Asp Leu Val Lys Ser Ile Arg Tyr Leu Val
65                  70                  75                  80

Gln Asp Phe Ala Ala Leu Thr Ile Leu Tyr Phe Ala Leu Pro Ala Phe
                85                  90                  95

Glu Tyr Phe Gly Leu Phe Gly Tyr Leu Val Trp Asn Ile Phe Met Gly
            100                 105                 110

Val Phe Gly Phe Ala Leu Phe Val Val Gly His Asp Cys Leu His Gly
        115                 120                 125

Ser Phe Ser Asp Asn Gln Asn Leu Asn Asp Phe Ile Gly His Ile Ala
    130                 135                 140

Phe Ser Pro Leu Phe Ser Pro Tyr Phe Pro Trp Gln Lys Ser His Lys
145                 150                 155                 160

Leu His His Ala Phe Thr Asn His Ile Asp Lys Asp His Gly His Val
                165                 170                 175

Trp Ile Gln Asp Lys Asp Trp Glu Ala Met Pro Ser Trp Lys Arg Trp
            180                 185                 190

Phe Asn Pro Ile Pro Phe Ser Gly Trp Leu Lys Trp Phe Pro Val Tyr
        195                 200                 205

Thr Leu Phe Gly Phe Cys Asp Gly Ser His Phe Trp Pro Tyr Ser Ser
    210                 215                 220

Leu Phe Val Arg Asn Ser Asp Arg Val Gln Cys Val Ile Ser Gly Ile
225                 230                 235                 240

Cys Cys Cys Val Cys Ala Tyr Ile Ala Leu Thr Ile Ala Gly Ser Tyr
                245                 250                 255

Ser Asn Trp Phe Trp Tyr Tyr Trp Val Pro Leu Ser Phe Phe Gly Leu
            260                 265                 270

Met Leu Val Ile Val Thr Tyr Leu Gln His Val Asp Asp Val Ala Glu
        275                 280                 285

Val Tyr Glu Ala Asp Glu Trp Ser Phe Val Arg Gly Gln Thr Gln Thr
    290                 295                 300

Ile Asp Arg Tyr Tyr Gly Leu Gly Leu Asp Thr Thr Met His His Ile
305                 310                 315                 320

Thr Asp Gly His Val Ala His His Phe Asn Lys Ile Pro His Tyr
                325                 330                 335

His Leu Ile Glu Ala Thr Glu Gly Val Lys Lys Val Leu Glu Pro Leu
            340                 345                 350

Ser Asp Thr Gln Tyr Gly Tyr Lys Ser Gln Val Asn Tyr Asp Phe Phe
        355                 360                 365

Ala Arg Phe Leu Trp Phe Asn Tyr Lys Leu Asp Tyr Leu Val His Lys
370                 375                 380

-continued

```
Thr Ala Gly Ile Met Gln Phe Arg Thr Thr Leu Glu Glu Lys Ala Lys
385                 390                 395                 400
Ala Lys
```

NON-HUMAN TRANSGENIC MAMMALS EXPRESSING AN N-3 DESATURASE GENE

This application claims priority from U.S. Ser. No. 60/275,222, filed Mar. 12, 2001, the contents of which are incorporated herein by reference in their entirety.

TECHNICAL FIELD

This invention relates to compositions and methods for altering the content of polyunsaturated fatty acids in mammalian cells.

BACKGROUND

Some of the work presented herein was supported by a grant from the National Institutes of Health (CA79553). The United States government may, therefore, have certain rights in the invention.

Polyunsaturated fatty acids (PUFAs) are fatty acids having 18 or more carbon atoms and two or more double bonds. They can be classified into two groups, n-6 or n-3, depending on the position (n) of the double bond nearest the methyl end of the fatty acid (Gill and Valivety, *Trends Biotechnol.* 15:401–409, 1997; Broun et al., *Annu. Rev. Nutr.* 19:197–216, 1999; Napier et al., *Curr. Opin. Plant Biol.* 2:123–127, 1999). The n-6 and n-3 PUFAs are synthesized through an alternating series of desaturations and elongations beginning with either linoleic acid (LA, 18:2n6) or α-linolenic acid (ALA, 18:3n3), respectively (Gill and Valivety, supra; Broun et al., supra; Napier et al., supra). The major end point of the n-6 pathway in mammals is arachidonic acid (AA, 20:4n6) and major end points of the n-3 pathway are eicosapentaenoic acid (EPA, 20:5n3) and docosahexaenoic acid (DHA, 22:6n3).

An important class of enzymes involved in the synthesis of PUFAs is the class of fatty acid desaturases. These enzymes introduce double bonds into the hydrocarbon chain at positions determined by the enzyme's specificity. Although, in most cases, animals contain the enzymatic activity to convert LA (18:2n6) and ALA (18:3n3) to longer-chain PUFA (where the rate of conversion is limiting), they lack the 12- and 15-desaturase activities necessary to synthesize the precursor (parent) PUFA, LA and ALA (Knutzon et al., *J. Biol. Chem.* 273:29360–29366, 1998). Furthermore, the n-3 and n-6 PUFA are not interconvertible in manmalian cells (Goodnight et al., *Blood* 58: 880–885, 1981). Thus, both LA and ALA and their elongation, desaturation products are considered essential fatty acids in the human diet. The PUFA composition of mammalian cell membranes is, to a great extent, dependent on dietary intake (Clandinin et al., *Can. J. Physiol. Pharmacol.* 63:546–556, 1985; McLennan et al., *Am. Heart J.* 116:709–717, 1988).

To the contrary, some plants and microorganisms are able to synthesize n-3 fatty acids such as ALA (18:3n-3) because they have membrane-bound 12- and 15-(n-3) desaturases that act on glycerolipid substrates in both the plastid and endoplasmic reticulum (Browse and Somerville, *Annu. Rev. Plant Physiol. Plant Mol. Biol.* 42: 467–506, 1991). Genetic techniques have led to the identification of the genes encoding the 12- and 15-desaturases from Arabidopsis thaliana and other higher plant species (Okuley et al., *Plant Cell* 6:147–158, 1994; Arondel et al., *Science* 258:1353–1355, 1992). Recently, a fat-1 gene encoding an n-3 fatty acid desaturase was cloned from *Caenorhabditis elegans* (Spychalla et al., *Proc. Natl. Acad. Sci. USA* 94:1142–1147, 1997; see also U.S. Pat. No. 6,194,167).

SUMMARY

The present invention is based, in part, on the discovery that the *C. elegans* n-3 desaturase gene, fat-1, can be successfully introduced into other types of animal cells (e.g., mammalian cells), where it quickly and effectively elevates the cellular n-3 PUFA content and dramatically balances the ratio of n-6:n-3 PUFAs. More specifically, heterologous expression of the fat-1 gene in rat cardiac myocytes rendered those cells capable of converting various n-6 PUFAs to the corresponding n-3 PUFA and changed the n-6:n-3 ratio from about 15:1 (an undesirable ratio) to 1:1 (a desirable ratio). In addition, an eicosanoid derived from n-6 PUFA (i.e. arachidonic acid) was significantly reduced in the trasgenic cells (as described further below, levels of arachidonic acid can be assessed to determine whether a given nucleic acid encodes a biologically active desaturase; similarly, one can assess the levels of n-6 PUFA; the levels of n-3 PUFA; and the ratio of n-6:n-3 PUFAs). Accordingly, the present invention features compositions (e.g., nucleic acids encoding fat-1, optionally and operably linked to a constitutively active or tissue-specific promoter) and methods that can be used to effectively modify the content of PUFAs in animal cells (i.e., cells other than those of *C. elegans*, for example, mammalian cells such as myocytes, neurons (whether of the peripheral or central nervous system), adipocytes, endothelial cells, and cancer cells). More generally, a fat-1 sequence or a biologically active variant thereof can be operably linked to a regulatory sequence. Regulatory sequences encompass not only promoters, but also enhancers or other expression control sequence, such as a polyadenylation signal, that facilitates expression of the nucleic acid. The modified cells (whether in vivo or ex vivo (e.g., in tissue culture)), transgenic animals containing them, and food products obtained from those animals (e.g., meat or other edible parts of the animals (e.g., liver, kidney, or sweetbreads)) are also within the scope of the present invention.

In one embodiment, the invention features mammalian cells that contain a nucleic acid sequence encoding the *C. elegans* n-3 desaturase or biologically active variants (e.g., fragments or other mutants) thereof. Biologically active variants of the n-3 desaturase enzyme are variants that retain enough of the biological activity of a wild-type n-3 desaturase to be therapeutically or clinically effective (i.e., variants that are useful in treating patients, producing transgenic animals, or conducting diagnostic or other laboratory tests). For example, variants of n-3 desaturase can be mutants or fragments of that enzyme that retain at least 25% of the biological activity of wild-type n-3 desaturase. For example, a fragment of an n-3 desaturase enzyme is a biologically active variant of the full-length enzyme when the fragment converts n-6 fatty acids to n-3 fatty acids at least 25% as efficiency as the wild-type enzyme does so under the same conditions (e.g., 30, 40, 50, 75, 80, 90, 95, or 99% as efficient as wild-type n-3 desaturase). Variants may also contain one or more amino acid substitutions (e.g., 1%, 5%, 10%, 20%, 25% or more of the amino acid residues in the wild-type enzyme sequence can be replaced with another amino acid residue). These substitutions can constitute conservative amino acid substitutions, which are well known in the art. Cells that express a fat-1sequence (optionally, operably linked to a constitutively active or tissue-specific promoter) are valuable aids to research because they provide a convenient system for characterizing the functional properties of the fat-1 gene and its product (cells in tissue culture are particularly convenient, but the invention is not so limited). They also allow one to study any cellular mechanism mediated by n-3 fatty acids without the lengthy feeding procedures of cells or animals that are currently required, and they serve as model systems that can be used, for example, to evaluate existing methods and to design new methods for effectively transferring sequences encoding an n-3 desaturase into cells in vivo. In any of these contexts (e.g. whether the compositions of the invention are being used to treat patients, to generate transgenic animals, or in cell culture assays), nucleic acids encoding fat-1 or a biologically active variant thereof can be co-expressed (by way of the same or a separate vector) with a heterologous gene. The heterologous gene can be, for example, another therapeutic gene (e.g., a receptor for a small molecule or chemotherapeutic agent) or a marker gene (e.g., a sequence encoding a fluorescent protein, such as green fluorescent protein (GFP) or enhanced (EGFP)).

The nucleic acids of the invention can be formulated for administration to a patient. For example, they can be suspended in sterile water or a physiological buffer (e.g., phosphate-buffered saline) for oral or parenteral administration to a patient (e.g., intravenous, intramuscular, intradermal, or subcutaneous injection (in the event the patient has a tumor, the compositions can be injected into the tumor or adminstered to the tissue surrounding the site from which a tumor was removed) or by inhalation).

The invention also features transgenic animals (including any animal kept as livestock or as a food source) that express the *C. elegans* n-3 desaturase gene or a biologically active variant thereof. Given the discovery that a *C. elegans* fat-1 gene can be efficiently expressed when delivered to a mammalian cell, this gene can be used to generate transgenic mice or larger transgenic animals (such as cows, pigs, sheep, goats, rabbits or any other livestock or domesticated animal) according to methods well known in the art. Depending on whether the construct used contains a constitutively active promoter or a tissue-specific promoter (e.g., a promoter that is active in skeletal muscle, breast tissue, the colon, neurons, retinal cells, pancreatic cells (e.g., islet cells) etc.) the fat-1 gene can be expressed globally or in a tissue-specific manner. The cells of the transgenic animals will contain an altered PUFA content that, as described further below, is more desirable for consumption. Thus, transgenic livestock (or any animal that is sacrificed for food) that express the desaturase enzyme encoded by the fat-1 gene will be superior (i.e., healthier) sources of food. Food obtained from these animals can be provided to healthy individuals or to those suffering from one or more of the conditions described below.

As noted, the invention features methods of treating patients (including humans and other mammals) who have a condition associated with an insufficiency of n-3 PUFA or an imbalance in the ratio of n-3:n-6 PUFAs by administering a nucleic acid encoding an n-3 desaturase or a biologically active variant thereof (e.g., a fragment or other mutant). Alternatively, one can administer the protein encoded. The methods can be carried out with patients who have an arrhythmia or cardiovascular disease (as evidenced, for example, by high plasma triglyceride levels or hypertension), cancer (e.g., breast cancer or colon cancer), inflammatory or autoimmune diseases (such as rheumatoid arthritis, multiple sclerosis, inflammatory bowel disease (IBD), asthma, chronic obstructive pulmonary disease, lupus, diabetes, Sjogren's syndrome transplantation, ankylosing spondylitis, polyarteritis nodosa, reiter's syndrome, and scleroderma), a malformation (or threatened malformation, as occurs in premature infants) of the retina and brain, diabetes, obesity, skin disorders, renal disease, ulcerative colitis, Crohn's disease, chronic obstructive pulmonary disease, or who are at risk of rejecting a transplanted organ. Given that fat-1 expression can also inhibit cell death (by apoptosis) in neurons, the methods of the invention can also be used to treat or prevent (e.g., inhibit the likelihood of, or the severity of) neurodegenerative diseases. Accordingly, the invention features methods of treating a patient who has (or who may develop) a neurodegenerative disease such as Parkinson's disease, Alzheimer's disease, Huntington's disease (HD), spinal and bulbar muscular atrophy (SBMA; also known as Kennedy's disease), dentatorubral-pallidoluysian atrophy, spinocerebellar ataxia type 1 (SCA1), SCA2, SCA6, SCA7, or Machado-Joseph disease (MJD/SCA3) (Reddy et al. *Trends Neurosc.* 22:248–255, 1999). As a balanced n-6:n-3 ratio is essential for normal growth and development, and as noted above, the methods of the invention can be advantageously applied to patients who have no discernable disease or condition.

Abbreviations used herein include the following: AA for arachidonic acid (20:4n-6); DHA for docosahexaenoic acid (22:6n-3); EPA for eicosapentaenoic acid (20:5n-3); GFP for green fluorescent protein; Ad.GFP for adenovirus carrying GFP gene; Ad.GFP.fat-1 for adenovirus carrying both fat-1 gene and GFP gene; and PUFAs for polyunsaturated fatty acids.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. All publications, patent applications, patents, and other references mentioned herein are incorporated by reference in their entirety. In case of conflicting subject matter, the present specification, including definitions, will control. In addition, the materials, methods, and examples are illustrative only and not intended to be limiting.

Other features and advantages of the invention will be apparent from the following detailed description, the drawings, and the Examples.

BRIEF DESCRIPTION OF THE DRAWINGS

FIG. 1 is a collection of four photomicrographs showing gene transfer efficiency. Rat cardiac myocytes were infected with Ad.GFP (left panels; control) or Ad.GFP.fat-1 (right panels). Forty-eight hours after infection, cardiomyocytes were visualized with bright light (upper panels) and at 510 nm of blue light (lower panels). Coexpression of GFP demonstrates visually that the transgene is being expressed in cells with a high efficiency.

FIG. 5 is a Table showing the polyunsaturated fatty acid composition of total cellular lipids from control cardiomyocytes and the transgenic cardiomyocytes expressing a *C. elegans* fat-1 cDNA.

FIG. 9 is a pair of partial gas chromatograph traces showing fatty acid profiles of total cellular lipids extracted from control neurons and neurons infected with Ad-GFP-fat-1.

FIG. 10 is a Table comparing the PUFA composition of total cellular lipids from rat cortical neurons (control) and transgenic cells expressing a *C. elegans* fat-1 cDNA (fat-1).

FIG. 13 is a pair of tracings showing differential responses of myocytes infected with Ad.GFP and myocytes infected with Ad.GFP.fat-1 to 7.5 mM extracellular calcium.

FIG. 15 is a table showing PUFA compositions of total cellular lipids from control MCF-7 cells and the transgenic MCF-7 cells expressing a *C. elegans* fat-1 cDNA.

FIGS. 17A and 17B are representations of the nucleotide sequence of the *C. elegans* fat-1 cDNA SEQ ID NO:3 and the deduced amino acid sequence of the Fat-1 polypeptide (SEQ ID NO: 4).

DETAILED DESCRIPTION

Figure 2:
FIG. 2 is an autoradiogram of a ribonuclease (RNase) protection assay of fat-1 transcript levels in cardiac myocytes infected with Ad.GFP (control) and myocytes infected with Ad.GFP.fat-1. Total RNA (10 µg) isolated from the cardiomyocytes was hybridized with anti-sense RNA probes, digested with RNase and resolved by electrophoresis through a denaturing polyacrylamide gel. The fat-1 mRNA was visualized by autoradiography. A probe targeting β-actin gene was used as control.

The studies described below demonstrate that, inter alia, a nucleic acid molecule encoding an n-3 desaturase can be efficiently expressed in a variety of mammalian cell types and, as a consequence, those cells produce significant amounts of n-3 PUFA from endogenous n-6 PUFA and have a more balanced ratio of n-6 to n-3 PUFA (1:1). The studies were carried out using recombinant adenoviral expression vectors, which can mediate gene transfer in vivo or in vitro. Adenoviral vectors expressing fat-1, or biologically active variants thereof, as well as other types of viral and non-viral expression vectors are within the scope of the invention now claimed. Other viral vectors that can be employed as expression constructs in the present invention include vectors derived from viruses such as vaccinia virus (e.g., a pox virus or a modified vaccinia virus ankara (MVA)), an adeno-associated virus (AAV), or a herpes viruses. These viruses offer several attractive features for various mammalian cells. For example, herpes simplex viruses (e.g., HSV-1) can be selected to deliver fat-1 or a biologically active variant thereof, to neuronal cells (and thereby treat patients with neurodegenerative conditions).

Other retroviruses, liposomes, and plasmid vectors are also well known in the art and can also be used (e.g., the expression vector pUR278 can be used when one wishes to fuse a fat-1 sequence to the lacZ gene; lacZ encodes the detectable marker β-galactosidase (see, e.g., Ruther et al., *EMBO J.*, 2:1791, 1983). A fat-1 sequence can also be fused to other types of heterologous sequences, such as a sequence that encodes another therapeutic gene or a sequence that, when expressed, improves the quantity or quality (e.g., solubility or circulating half-life) of the fusion protein. For example, pGEX vectors can be used to express the proteins of the invention fused to glutathione S-transferase (GST). In general, such fusion proteins are soluble and can be easily purified from lysed cells by adsorption to glutathione-agarose beads followed by elution in the presence of free glutathione. The pGEX vectors (Pharmacia Biotech Inc; Smith and Johnson, *Gene* 67:31–40, 1988) are designed to include thrombin or factor Xa protease cleavage sites so that the cloned target gene product can be released from the GST moiety. Other fusion partners include albumin and a region (e.g., the Fc region) of an immunoglobulin molecule (e.g., IgG, IgA, IgM, or IgE). Other useful vectors include pMAL (New England Biolabs, Beverly, Mass.) and pRIT5 (Pharmacia, Piscataway, N.J.), which fuse maltose E binding protein and protein A, respectively, to an n-3 desaturase.

Transgene expression can be sufficiently prolonged from episomal systems, so that readministration of the vector, with its transgene, is not necessary. Alternatively, the vector can be designed to promote integration into the host genome, preferably in a site-specific location, which would help ensure that the transgene is not lost during the cell's lifetime. Whatever the means of delivery, transcriptional control, exerted by the host cell, would promote tissue specificity and regulate transgene expression.

The expression vector will be selected or designed depending on, for example, the type of host cell to be transformed and the level of protein expression desired. For example, when the host cells are mammalian cells, the expression vector can include viral regulatory elements, such as promoters derived from polyoma, Adenovirus 2, cytomegalovirus and Simian Virus 40. The nucleic acid inserted (i.e., the sequence to be expressed; here, fat-1) can also be modified to encode residues that are preferentially utilized in *E. coli* (Wada et al., *Nucleic Acids Res.* 20:2111–2118, 1992). These modifications can be achieved by standard recombinant techniques. More generally, the expression vectors of the invention can be designed to express proteins in prokaryotic or eukaryotic cells. For example, polypeptides of the invention can be expressed in bacterial cells (e.g., *E. coli*), fungi, yeast, or insect cells (e.g., using baculovirus expression vectors). For example, a baculovirus such as Autographa californica nuclear polyhedrosis virus (AcNPV), which grows in *Spodoptera frugiperda* cells, can be used as a vector to express foreign genes.

As noted elsewhere, the expression vectors and nucleic acids used to express fat-1 can also contain a tissue-specific promoter. Such promoters are known in the art and include, but are not limited to liver-specific promoters (e.g., albumin; Miyatake et al., 1997), muscle-specific promoters (e.g., myosin light chain 1 (Shi et al., 1997) α-actin), pancreatic-specific promoter (e.g., insulin or glucagon promoters), neural-specific promoters (e.g., the tyrosine hydroxylase promoter or the neuron-specific enolase promoter), endothelial cell-specific promoters (e.g., von Willebrandt; Ozaki et al., 1996), and smooth muscle-cells specific promoters (e.g., 22a; Kim et al., 1997). Tumor-specific promoters are also being used in developing cancer therapies, including tyrosine kinase-specific promoters for B16 melanoma (Diaz et al., 1998), DF3/MUC1 for certain breast cancers (Wen et al., 1993; for breast cancer, an adipose-specific promoter region of human aromatase cytochrome p450 (p450arom) can also be used (see U.S. Pat. No. 5,446,143; Mahendroo et al., *J. Biol. Chem.* 268:19463–19470, 1993; and Simpson et al., *Clin. Chem.* 39:317–324, 1993). An α-fetoprotein promoter can be used to direct expression in hepatomas (Chen et al., 1995). The vectors and other nucleic acid molecules of the invention (e.g., the fat-1 cDNA per se) can also include sequences that limit the temporal expression of the transgene. For example, the transgene can be controlled by drug inducible promoters by, for example including cAMP response element enhancers in a promoter and treating the transfected or infected cell with a cAMP modulating drug (Suzuki et al., 1996). Alternatively, repressor elements can prevent transcription in the presence of the drug (Hu et al., 1997). Spatial control of expression has also been achieved by using ionising radiation (radiotherapy) in conjunction with the erg1 gene promoter (Hallaham et al., 1995). Constructs that contain such regulatory sequences are within the scope of the present invention.

In the examples that follow, RNA analysis and enzymatic assays were performed to assess gene expression, and gas chromatography-mass spectrometry were used to determine fatty acid profiles (these are standard techniques that one of ordinary skill in the art could use to assess any variant of the fat-1 sequence for biological activity; or incorporate in any method of assessing a sample obtained from a patient for fat-1 expression).

Some of the studies described below were conducted using cortical neurons. Fat-1 expression not only modified the cellular n-6:n-3 fatty acid ratio and eicosanoid profile in these neurons, but also protected the cells from apoptosis, thereby increasing cellular viability. More specifically, fat-1expression modified the fatty acid ratio and protected rat cortical neurons against growth factor withdrawal-induced apoptotis in the absence of supplementation with exogenous n-3 PUFAs. Accordingly, the nucleic acid molecules (and other compositions) described herein can be used as neuroprotectants, which can be administered to premature infants and to older patients having any neurodegenerative disease (alternatively, the molecules or other compositions can be delivered to an animal, parts of which are then consumed by the patient). The protective effect of gene transfer on neuronal apoptosis minics the protective effects of n-3 fatty acid supplementation.

The positive results obtained with neurons are especially encouraging because n-3 PUFA deficiency leads to abnormal development of the retina and the brain, particularly in premature infants (Uauy et al., *Lipids* 36:885–895, 2001), and animals deficient in n-3 PUFA show deficits in memory, spatial and context-dependent learning, and loss of visual acuity (Carrie et al., *Neurosci. Lett.* 266:69–72, 1999; Yehuda et al., *J. Neurosci. Res.* 56:565–70, 1999). There are also indications that various neurological disease states in humans are associated with an n-3 deficient status (Vancassel et al., *Prost. Leuk. Ess. Fatt. Acids* 65:1–7, 2001; Hoffman and Birch, *World Rev. Nutr. Diet* 83:52–69, 1998).

The biological functions of PUFAs are described further here, as these functions bear on the types of conditions amenable to treatment with the nucleic acid molecules (and other compositions) described herein. PUFAs are important structural components of membrane phospholipids and are precursors of families of signaling molecules (eicosanoids) including prostaglandins, thromboxanes, and leukotrienes (Needleman et al., *Ann. Rev. Biochem.* 55:69–102, 1986; Smith and Borgeat, In *Biochemistry of Lipids and Membranes*, D. E. Vance & J. E. Vance, Eds., Benjamin/Cummings, Menlo Park, Calif., 00 325–360, 1986). The eicosanoids derived from PUFAs play a key role in modulating inflammation, cytokine release, the immune response, platelet aggregation, vascular reactivity, thrombosis and allergic phenomena (Dyerberg et al., *Lancet* 2:117–119, 1978; Cyerberg and Bang, *Lancet* 2:433–435, 1979; James et al., *Am. J. Clin Nutr.* 7:343S-3438S, 2000; Calder, *Ann. Nutr. Metab.* 41:203–234, 1997). The principal fatty acid precursors of these signaling compounds are arachidonic acid (AA, 20:4n6), providing an n-6 substrate that is responsible for the major synthesis of the series 2 compounds, and eicosapentaenoic acid (EPA, 20:5n3), an n-3 substrate that is responsible for the parallel synthesis of many series 3 eicosanoids with an additional double bond. The n-6:n-3 ratio in phospholipids modulates the balance between eicosaniods of the 2 and 3 series derived from AA and EPA. The eicosanoids derived from AA (series 2) and EPA (series 3) are functionally distinct and some have important opposing physiological functions (Dyerberg et al., *Lancet* 2:117–119, 1978; Cyerberg and Bang, *Lancet* 2:433435, 1979; James et al., *Am. J. Clin Nutr.* 7:343S–3438S, 2000; Calder, *Ann. Nutr. Metab.* 41:203–234, 1997). Series 3 eicosanoids are weak agonists or, in some cases, antagonists of series 2 eicosanoids. For example, eicosanoids of the 2 series promote inflammation and platelet aggregation, and activate the immune resoponse, whereas series 3 eicosanoids tend to ameliorate these effects. In addition, PUFAs, in the form of free fatty acids, are involved in gene expression and intercellular cell-to-cell communication (Price et al., *Curr. Opin. Lipidol* 11:3–7,2000; Sellmayer et al. *Lipids* 31 Suppl: S37–S40, 1996; vonSchacky, *J. Lab. Clin. Med.* 128:5–6, 1996). Thus, PUFA can exhibit many diverse biological effects.

The compositions and methods described herein can be used to treat a variety of specific conditions as well as to improve general health. Any condition that is amenable to treatment by administration of n-3 PUFAs is amenable to treatment by way of the methods of the present invention, which comprise administration of a gene encoding an n-3 desaturase (e.g., the *C. elegans* fat-1 gene). Some of the conditions amenable to treatment are described below.

n-3 PUFAs have attracted considerable interest as pharmaceutical and nutraceutical compounds (Connor, *Am. J. Clin. Nutr.* 70:560S–569S, 1999; Simopoulos, *Am. J. Clin. Nutr.* 70:562S–569S, 1999; Salem et al., *Lipids* 31:S1-S326, 1996). During the past 25 years, more than 4,500 studies have explored the effects of n-3 fatty acids on human metabolism and health (e.g., cardiovascular health). From epidemiology to cell culture and animal studies to randomized controlled trials, the cardioprotective effects of omega-3 fatty acids have been recognized (Leaf and Kang, *World Rev. Nutr. Diet.* 83:24–37, 1998; De Caterina et al., Eds., n-3 *Fatty Acids and Vascular Disease*, Springer-Verlag, London, 1999, pp 166; O'Keefe and Harris, *Mayo Clin. Proc.* 75:607–614, 2000). The predominant beneficial effects include a reduction in sudden death (Albert et al., *JAMA* 279:23–28, 1998; Siscovick et al., *JAMA*

274:1363–1367, 1995), decreased risk of arrhythmia (Kang and Leaf, *Circulation* 94:1774–1780, 1996), lower plasma triglyceride levels (Harris, *Am. J. Clin. Nutr.* 65:1645S–1654S, 1997), and a reduced blood-clotting tendency (Agren et al., *Prostagland. Leukot. Esseizt. Fatty Acids* 57:419–421, 1997; Mori et al., *Arterioscler. Throm. Basc. Biol.* 17:279–286, 1997). Evidence from epidemiological studies shows that another n-3 fatty acid, α-linolenic acid, reduces risk of myocardial infarction (Guallar et al., *Arterioscler. Thromb. Vasc. BioL* 19:1111–1118, 1999) and fatal ischemic heart disease in women (Hu et al., *Am. J. Clin. Nutr.* 69:890–897, 1999). Several randomized controlled trials recently have demonstrated beneficial effects of both α-linolenic acid (de Lorgeril et al., *Circulation* 99:779–785, 1999) and marine ω-3 fatty acids (Singh et al., *Cardiovasc. drugs ther.* 11:485–491, 1997; Von Schacky et al., *Ann. Intern. Med.* 130:554–562, 1999; GISSI-Prevenzione Investigators, *Lancet* 354:447–455, 1999) on both coronary morbidity and mortality in patients with coronary disease. The n-3 fatty acid, EPA, exerts anticancer activity in vitro and in animal models of experimental cancer (Bougnoux, *Curr. Opin. Clin. Nutr. Metab. Care* 2:121–126, 1999; Cave, *Breast Cancer Res. Treat.* 46:239–246, 1997). Human studies show that populations whose diets are rich in EPA exhibit a remarkably low incidence of cancer (Rose and Connolly, *Pharmacol. Ther.* 83:217–244, 1999). Supplementation with n-3 PUFAs shows therapeutic effects on inflammatory and autoimmune diseases such as arthritis (Kremer, *Am. J. Clin. Nutr.* 71:349S–351 S, 2000; Ariza-Ariza et al., *Semin. Arthritis Rheum.* 27:366–370, 1998; James et al., *Am. J. Clin. Nutr.* 71:343S–348S), and studies with nonhuman primates (Neuringer et al., *Proc. Natl. Acad. Sci. USA* 83:4021–4025, 1986) and human newborns (Uauy et al., *Proc. Nutr. Soc.* 59:3–15, 2000; Uauy et al., *Lipids* 31:S167–176, 1996) indicate that the n-3 fatty acid, DHA, is essential for the normal fimctional development of the retina and brain, particularly in premature infants. Furthermore, n-3 PUFA have been shown to have beneficial effects on many other clinical problems, such as hypertension (Appel et al., *Arch. Intern. Med.* 153:1429–1438, 1993), diabetes (Raheja et al., *Ann. N.Y. Acad. Sci.* 683:258–271, 1993), obesity (Clarke, *Br. J. Nutr.* 83:S59–66, 2000), skin disorders (Ziboh, *World Rev. Nutr. Diet.* 66:425–435, 1991), renal disease (De Caterina et al., *Kidney Int.* 44:843–850, 1993), ulcerative colitis (Stenson et al., *Ann. Intern. Med.* 116: 609–614, 1992), Crohn's disease (Belluzzi et al., *N. Engl. J. Med.* 334:1557–1560, 1996), chronic obstructive pulmonary disease (Shahar et al., *N. Engl. J. Med.* 331:228–233, 1994), and transplanted organ rejection (Otto et al., *Transplantation* 50:193–198, 1990). In general, a balanced n-6:n-3 ratio of the body lipids is essential for normal growth and development and plays an important role in the prevention and treatment of many clinical problems. The diseases, disorders, and conditions described above are amenable to treatment with the nucleic acid molecules (and other compositions) described herein.

According to recent studies (Simopoulos, *Poultry Science* 79:961–970, 2000), the ratio of n-6 to n-3 essential fatty acids in today's diet is around 10–20:1. This indicates that present Western diets are deficient in n-3 fatty acids compared with the diet on which humans evolved and their genetic patterns were established (n-6/n-3=1:1) (Leaf and Weber, *Am. J. Clin Nutr.* 45:1048–1053, 1987). Since the n-6 and n-3 fatty acids are metabolically and functionally distinct and have important opposing physiological functions, their balance is important for homeostasis and normal development. However, n-3 and n-6 PUFAs are not interconvertible in the human body because mammalian cells lack the enzyme n-3 desaturase. Therefore, the balance between n-6 and n-3 PUFA in biological membranes is regulated based on dietary supply. Elevating the tissue concentrations of n-3 fatty acids in human subjects or animals relies on increased consumption of n-3 PUFA-enriched foods or n-3 PUFA supplements. Given the potential therapeutic actions of n-3 PUFAs, an international scientific working group has recommended diets in which the intake of n-6 fatty acids is decreased and the intake of n-3 fatty acids is increased (Simopoulos, *Food Australia* 51:332–333, 1999). The American Heart Association has also recently made such a dietary recommendation (AHA Dietary Guidelines: Revision 2000, *Circulation* 102:2284–2299, 2000).

Although dietary supplementation with n-3 PUFA is a safe intervention, it has a number of limitations. For example, to achieve a significant increase in tissue concentrations of n-3 PUFA in vivo requires a chronic intake of high doses of n-3 PUFA for a period of at least 2–3 months. Bioavailability of fatty acids to cells from the diet involves a series of physiological processes including digestion, absorption, transport and metabolism of fat. Thus, the efficacy of dietary intervention depends on the physiological and health status of an individual. A patient in critical condition or who has a gastrointestinal disorder is unlikely to be able to ingest or absorb fatty foods or n-3 PUFA supplements. In addition, encapsulated fish oil supplements are unlikely to be suited to daily use over a person's lifetime because of their high caloric content. Moreover, ingestion of some species of fish from costal waters and lakes may carry toxic amounts of mercury or organic toxins, and effective dietary intervention requires a disciplined change in dietary habits that some people may not be able to sustain. In view of the foregoing, there is a great need for the means to quickly and effectively increase cellular n-3 PUFA content and balance the n-6:n-3 ratio without resorting to long-term intake of fish or fish oil supplements. This need is met by the methods of the present invention, which create an alternative food source (via transgenic livestock whose cells contain substantially more n-3 PUFAs than in non-transgenic animals) or which provide for administration of a gene encoding an n-3 desaturase enzyme to patients (e.g., human patients). A particular advantage of the present methods is that they not only elevate tissue concentrations of n-3 PUFAs, but also simultaneously decreases the levels of excessive endogenous n-6 PUFA.

EXAMPLES

Example 1

Construction of a Recombinant Adenovirus

A recombinant adenovirus carrying the fat-1 gene was constructed following procedures similar to those described by He et al. (*Proc. Natl. Acad. Sci. USA* 95:2509–2514, 1998). The n-3 fatty acid desaturase cDNA (fat-1 gene) in pCE8 was kindly provided by Dr. J. Browse (Washington State University) (but can be synthesized or cloned using information and techniques available to those of ordinary skill in the art; see Spychalla et al., *Proc. Natl. Acad. Sci. USA* 94:1142–1147, 1997; U.S. Pat. No. 6,194,167; and FIGS. 17A and 17B). The cDNA insert of pCE8 was excised from the plasmid with an EcoRI/KpnI double digest, inserted into a shutter vector, and then recombined with an adenoviral backbone according to the methods of He et al. (supra). Two, first-generation type 5 recombinant adenoviruses were generated: Ad.GFP, which carries the green fluorescent protein (GFP, as reporter gene) under control of the cytomegalvirus (CMV) promoter, and Ad.GFP.fat-1, which carries both the fat-1 and GFP genes, each under the control of separate CMV promoters. The recombinant viruses were prepared as high titer stocks through propagation in 293 cells, as described previously (Hajjar et al. *Circulation* 95:423–429, 1997). The constructs were confirmed by enzymatic digestion and by DNA sequence analysis. See also Hajjar et al., *Circulation* 95:4230429, 1997 and Hajjar et al., *Circ. Res.* 81:145–153, 1997.

Wild-type adenovirus contamination can be assessed and shown to be excluded by the absence of both PCR-detectable E1 sequences and cytopathic effects on the nonpermissive A549 cell line. Alternative adenoviral vectors with other promoters or adeno-associated viral (AAV) vectors can be constructed if necessary or desired.

Example 2

Culture and Infection of Cardiac Myocytes with Adenovirus

Cardiac myocytes were isolated from one-day-old rats using the National Cardiomyocyte Isolation System (Worthington Biochemical Corp., Freehold, N.J.). The isolated cells were placed in 6-well plates and cultured in F-10 medium containing 5% fetal bovine serum and 10% horse serum at 37° C. in a tissue culture incubator with 5% $CO_2$ and 98% relative humidity. Cells were used for experiments after 2–3 days of culture. Viral infection was carried out by adding viral particles at different concentrations ($5 \times 10^{9-10^{10}}$ pfu) to culture medium containing 2% fetal bovine serum (FBS). After a 24 hour incubation, the infection medium was replaced with normal (15% serum), culture medium supplemented with 10 µM of 18:2n-6 and 20:4n-6. About 48 hours after infection, the cells can be used (e.g., one can then analyze gene expression, fatty acid composition, viability, or growth (e.g., proliferation or rate of division)).

Example 3

Detecting Fat-1 Expression with Fluorescence Microscopy and RNA Analysis

Gene expression can be assessed by many methods known in the art of molecular biology. Here, expression of fat-1 in cardiac myocytes, infected as described above, was assessed by visual examination of infected cells and a ribonuclease (RNase) protection assay.

More specifically, the coexpression of GFP allowed us to identify the cells that were infected and expressed the transgene. About 48 hours after infection, almost all of the cells (>90%) exhibited bright fluorescence, indicating a high efficiency of gene transfer and a high expression level of the transgene (see FIG. 1). Expression of fat-1 transcripts was also determined by RNase protection assay using a RPA III™ it (Ambion). Briefly, total RNA was extracted from cultured cells using an RNA isolation kit (Qiagen) according to the manufacturer's protocol. The plasmid containing the fat-1 gene, pCE8, was linearized and used as a transcription template. Anti-sense RNA probes were transcribed in vitro using $^{33}$P-UTP, hybridized with the total RNA extracted from the myocytes, and digested with RNase to remove non-hybridized RNA and probe. The protected RNA:RNA was resolved by electrophoresis through a denaturing gel and subjected to autoradiography. A probe targeting the β-actin gene was used as a control. Fat-1 mRNA was not detected in cells infected with AD.GFP (also used as a control), but was abundant in cells infected with Ad.GFP-.fat-1 (FIG. 2). This result indicates that adenovirus-mediated gene transfer confers very high expression of fat-1 gene in rat cardiac myocytes that normally lack the gene.

Example 4

Lipid Analysis; The Effect of n-3 Sesaturase on Fatty Acid Composition

By lipid analysis, one can determine whether the expression of a fat-1 gene in cardiac myocytes (or any other cell type) converts n-6 fatty acids to n-3 fatty acids and, thereby, changes the fatty acid composition of the cell. Following infection with the adenoviruses described above, cells were incubated in medium supplemented with n-6 fatty acids (10 µM 18:2n-6 and 10 µM 20:4n-6) for 2–3 days. After the incubation, the fatty acid composition of total cellular lipids was analyzed as described previously (Kang et al., *Biochim. Biophys. Acta.* 1128:267–274, 1992; Weylandt et al., *Lipids* 31:977–982, 1996).

Lipid was extracted with chloroform/methanol (2:1, v/v) containing 0.005% butylated hydroxytoluene (as antioxidant). Fatty acid methyl esters were prepared using 14% BF3/methanol reagent. Fatty acid methyl esters are quantified by GC/MS using a HP5890 Series II gas chromatograph equipped with a Supelcowax SP-10 capillary column attached to a HP-5971 mass spectrometer. The injector and detector are maintained at 260° C. and 280° C., respectively. The oven program is initially maintained at 150° C. for 2 minutes, then ramped to 200° C. at 10° C./min and held for 4 minutes, ramped again at 5° C./min to 240° C., held for 3 minutes, and finally ramped to 270° C. at 10° C./min and maintained for 5 minutes. Carrier gas flow rate is maintained at a constant 0.8 mL/min throughout. Total ion monitoring is performed, encompassing mass ranges from 50–550 amus. Fatty acid mass is determined by comparing areas of various analyzed fatty acids to that of a fixed concentration of internal standard.

Figure 3:
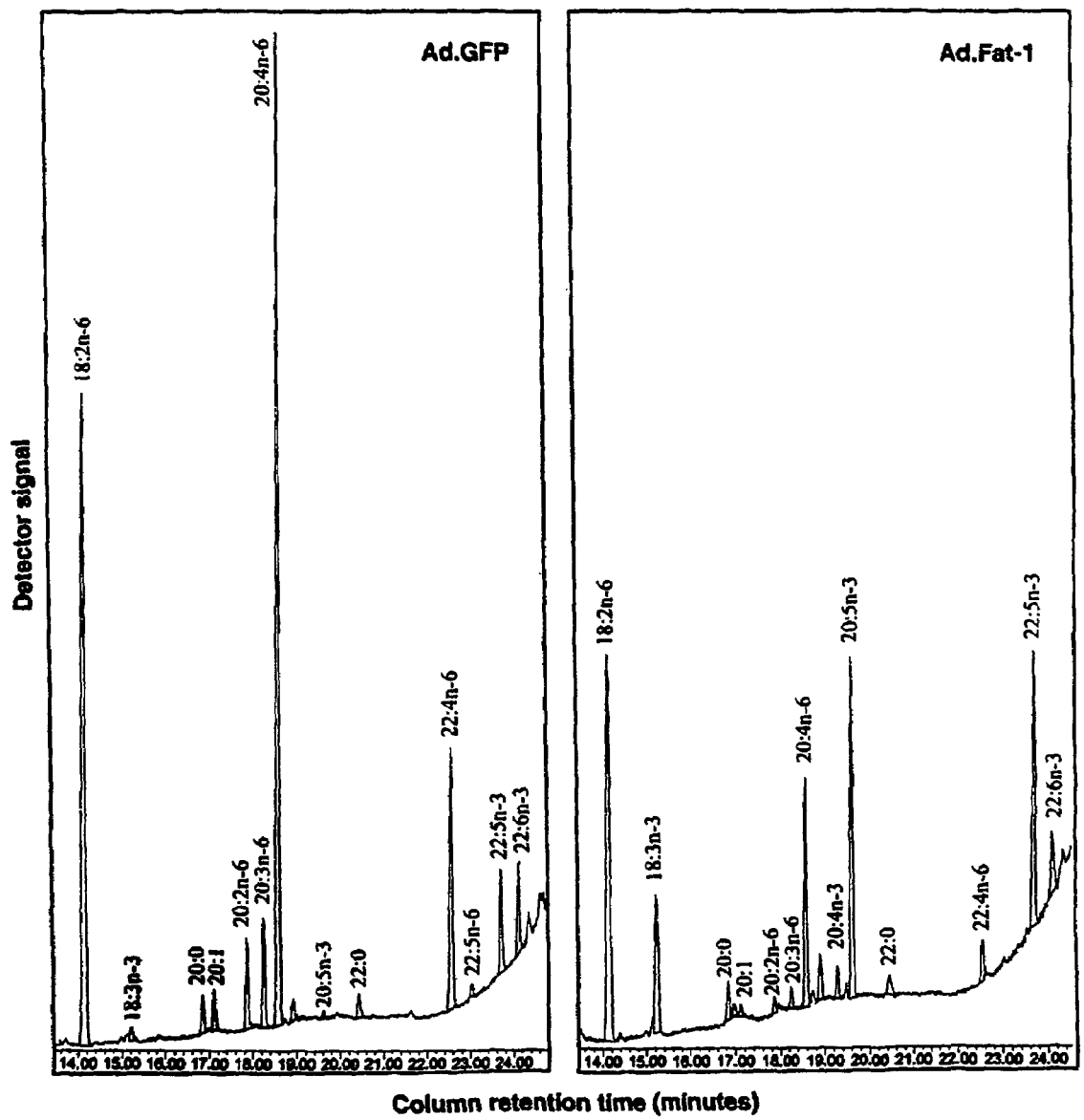
FIG. 3. is a pair of partial gas chromatograph traces showing fatty acid profiles of total cellular lipids extracted from control cardiomyocytes infected with Ad.GFP and cardiomyocytes infected with Ad.GFP.fat-1.

The fatty acid profiles were remarkably different between the control cells infected with Ad.GFP and the cells infected with Ad.GFP.fat-1 (FIG. 3). Moreover, cells infected with Ad.GFP showed no change in their fatty acid profiles when compared with non-infected cells. In the cells expressing the fat-1 gene (n-3 desaturase), almost all kinds of n-6 fatty acids were largely converted to the corresponding n-3 fatty acids, namely, 18:2n-6 to 18:3n-3, 20:2n-6 to 20:3n-3, 20:3n-6 to 20:4:n-3, 20:4n-6 to 20:5n-3, and 22:4n-6 to 22:5n-3. As a result, the fatty acid composition of the cells expressing fat-1 was significantly changed with respect to that of the control cells infected with Ad.GFP (FIG. 5). Importantly, the ratio of n-6:n-3 was reduced from 15:1 in the control cells to 1:1.2 in the cells expressing the n-3 fatty acid desaturase.

Example 5

Measuring Eicosanoids Following Fat-1 Expression

Figure 4:
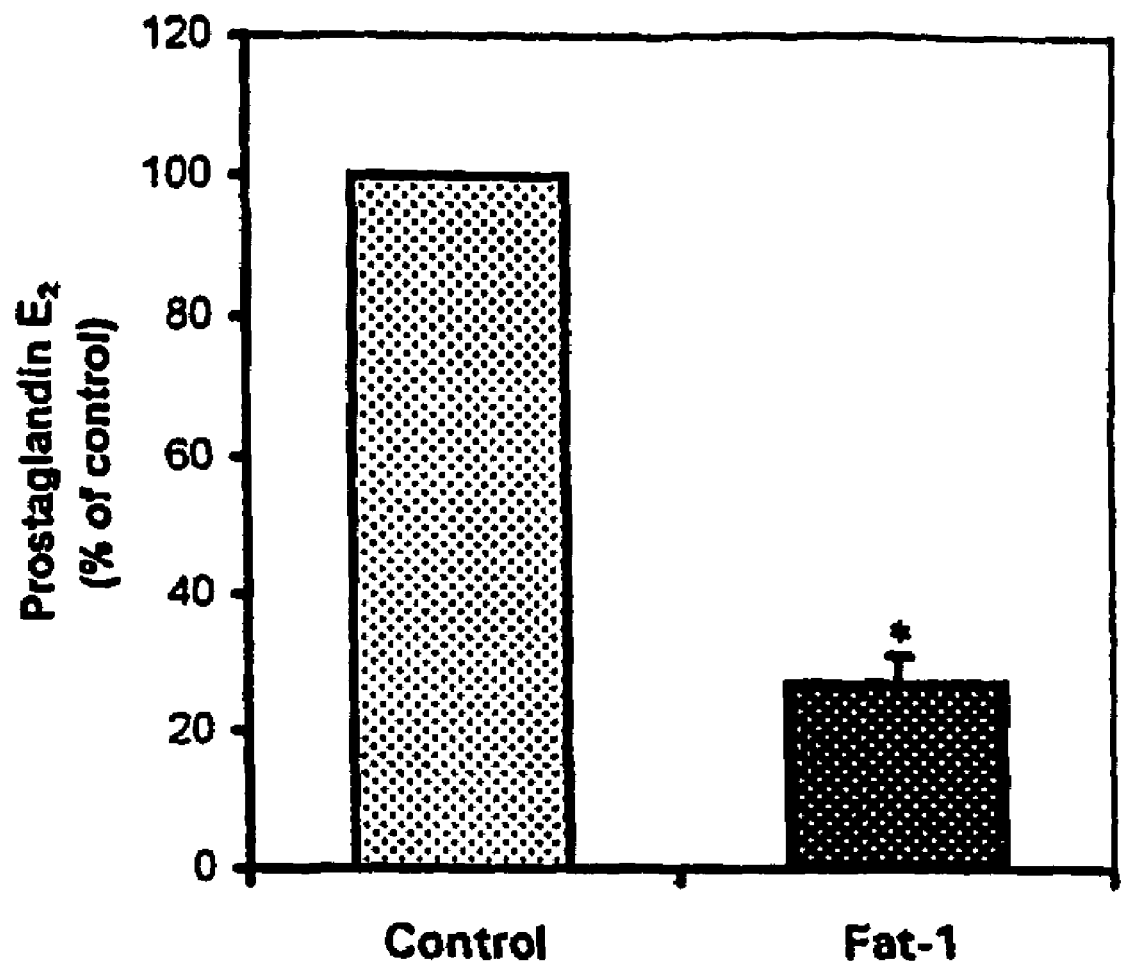
FIG. 4 is a bar graph depicting prostaglandin $E_2$ levels in control cardiomyocytes and cardiomyocytes expressing the fat-1 gene (as determined by enzyme immunoassay). Values are means ±SDs of three experiments and are expressed as % of control. *p<0.01.

Since 20:4n-6 (AA) and 20:5n-3 (EPA) are the precursors of 2-series and 3-series of eicosanoids, respectively, differences in the contents of AA and EPA may lead to a difference in production of eicosanoids in the cells. Thus, we measured the production of eicosanoids in the infected cells following stimulation with calcium ionophore A23187 by using a EIA kit that specifically detect prostaglandin $E_2$ with a 16% cross-reactivity with prostaglandin E3. More specifically, Prostaglandin $E_2$ was measured by using enzyme immunoassay kits (Assay Designs, Inc) following the manufacturer's protocol. (The cross-reactivity with PGE3 is 16%). Cultured cells were washed and serum-free medium containing calcium ionophore A23187 (5 µM). After a 10 minute incubation, the conditioned medium was recovered and subjected to eicosanoid measurement. The amount of prostaglandin $E_2$ produced by the control cells was significantly higher than that produced by cells expressing the n-3 desaturase encoded by fat-1 (FIG. 4).

Example 6

Analysis of Animal Cells in Culture

In this example and the two that follow, we set out three different experimental models: cultured cells (other types of cultured cells are tested further below), adult rats, and transgenic mice. As shown above, the cultured cell model can be used to characterize the enzymatic properties and biochemical effects of the n-3 desaturase when expressed in mammalian cells in vitro; the adult rat model can be used to evaluate the efficacy with which a transferred fat-1 gene can elevate tissue concentrations of n-3 PUFA in vivo, and the transgenic mouse model can be used to assess the long-term and systematic effects of the transgene on lipid composition of various tissues or organs in vivo. For the first two models, the introduction of the fat-1 gene into mammalian cells/ tissues will be carried out by mean of adenoviral gene transfer (mediated by recombinant adenoviruses). For the last model, gene transfer will be carried out by microinjection of the transgene into fertilized mouse eggs. Following gene transfer, the expression profile of the transferred gene can be characterized by mRNA and/or protein analysis (see, e.g., Example 3, above), and the biochemical effects, mainly the fatty acid composition of the cells or tissues, will be determined by GC-MS technology (see, e.g., Example 4, above). Eicosanoids will be measured by enzyme immunoassay (see, e.g., Example 5). Changes are identified by comparing the data obtained from fat-1-expressing cells with data obtained from control cells or tissues infected with the same (or a similar) virus, but not transfected with fat-1. The end point of these studies is the biochemical changes in cellular fatty acid composition and eicosanoid profile.

Figure 6:
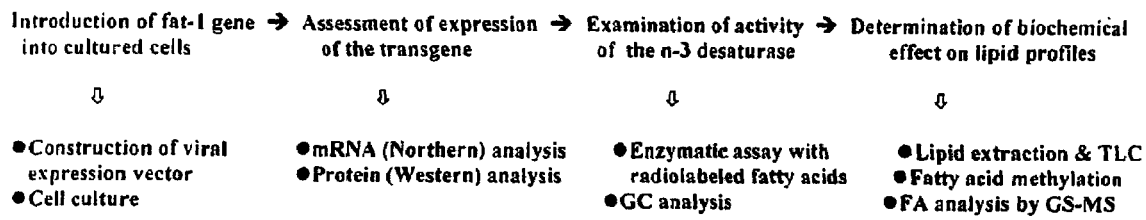
FIG. 6 is a flowchart of an experimental protocol.

Cultures of virtually any animal cells (including human cell lines) can be infected with recombinant adenovirus (Ad.GFP.fat-1 or Ad.GFP), after which expression of the transferred gene can be assessed by RNA or protein analysis. The experimental procedures and related methods are described in the Examples above and outlined in FIG. 6. Various cell types including cardiac myocytes, neurons, hepatocytes, endothelial cells, and macrophages have been used in studies of n-3 fatty acids.

Cardiac myocytes can be isolated and cultured as described above (see Example 2), and other cell types, such as cerebellar granule neurons and hepatocytes can be prepared from 1–5 day-old rats following the method described by Schousboe et al. (In *A Dissection and Tissue Culture Manual of the Nervous System*, Shahar et al., Eds., Alan R. Liss, New York, N.Y., pp. 203–206, 1989). Human cell lines, including breast cancer cell lines and leukemia cell lines can be cultured in MEN medium or RPMI 1640 supplemented with 10% fetal bovine serum (FBS) in a 37° C./5% $CO_2$ incubator.

Viral infection can be carried out by adding viral particles at various concentrations (e.g., $2\times10^{9-2\times10^{10}}$ pfu) to culture medium containing no FBS or 2% FBS (see also Example 2). ARer a 24-hour incubation, the infection medium is replaced with normal (10% FBS) culture medium. Forty-eight hours after infection, cells can be used for analysis of gene expression or fatty acid composition. Transgene expression can be assessed by fluorescence microscopy when a fluorescent tag is included in the transgene (see Example 1 and FIG. 1; similarly, the tag can be an antigenic protein detected by a fluorescent antibody) or by a standard RNA assay (e.g. a Northern blot or RNase protection assay). Since the fat-1 gene normally does not exist in control cells, it is not difficult to identify the difference in fat-1 mRNA between the control cells and cells expressing fat-1.

n-3 desaturase catalyzes the introduction of an n-3 double bond into n-6 fatty acids, leading to formation of n-3 fatty acids with one more double bond than their precursor n-6 fatty acids (e.g., 18:2n-6→18:3n-3, 20:4n-6→20:5n-3). The rate of conversion of substrates to products (the amount of products formed within a given time period) is thought to be directly proportional to the expression/activity of a desaturase. Thus, the functional activity of this enzyme can be determined, from a sample obtained from an animal (e.g., a tissue sample) or in cultured cells by measurement of the conversions (the quantity of products) using the following methods.

Fatty acid desaturation assay using radiolabeled n-6 fatty acids as substrates: The assay can be performed following the protocol described by Kang et al. (*Biochim. Biophys Acta.* 1128:267–274, 1992). Briefly, various labeled n-6 fatty acids (e.g., [$^{14}$C]18:2n-6, [$^{14}$C]20:4n-6) bound to BSA are added to serum-free culture medium and incubated with cells for 4–6 hours. After that, cells and culture medium will be harvested. Lipids are extracted and methylated (see below). The labeled fatty acid methyl esters are separated according to degree of unsaturation (i.e., the number of double bond) on silica-gel TLC plates impregnated with $AgNO_3$. Bands containing fatty acids with different double bonds can be identified by comparison with reference standards. Quantity of the labeled fatty acids is determined by scintillation counting, and data are compared between control cells and the cells expressing the fat-1 gene.

Fatty acid analysis by gas chromatography: Conversion of fatty acids can be determined more accurately by analysis of fatty acid composition using gas chromatography-mass spectrometry (see below). Using this method, no radiolabeled fatty acid is required. Fatty acid contents of cultured cells expressing the n-3 desaturase gene, in the presence of various substrates, can be analyzed. The conversion of each fatty acid can be determined by comparison of fatty acid profiles between control cells and the cells expressing the fat-1 gene.

The fatty acid composition of total cellular lipids or phospholipids can be analyzed as described previously (Kang et al., *Biochim. Biophys. Acta.* 1128:267–274, 1992; Weylandt et al., *Lipids* 31:977–982, 1996). The procedures are as follows:

Lipid extraction (see also Example 4): Five ml of chloroform/methanol (2:1, v/v) containing 0.005% butylated hydroxytoluene (as antioxidant) is added to washed cell pellets and vortexed vigorously for 1 minute then left at 4° C. overnight. One ml of 0.88% NaCl is added and mixed again. The chloroform phase containing lipids is collected. The remains are extracted once again with 2 ml chloroform. The chloroform is pooled and dried under nitrogen and stored in sealed tubes at −70° C.

Separation of lipids by thin-layer chromatography (TLC): TLC plates are activated at 100° C. for 60 minutes. TLC tanks are equilibrated with solvent for at least one hour prior to use. Total phospholipid and triacyglycerol are separated by running the sample on silica-gel G plates using a solvent system comprised of petroleum ether/diethyl ether/acetic acid (80:20:1 by vol.) for 30–35 minutes. Individual phospholipids are separated by TLC on silica-gel H plates using the following solvent system: chloroform/methanol/2-propanol/0.25% KCl/triethylamine (30:9:25:6:18 by vol.). Bands containing lipids are made visible with 0.01% 8-anilino-1-naphthalenesulfonic acid, and gel scrapings of each lipid fraction are collected for methylation.

Fatty acid methylation: Fatty acid methyl esters are prepared using 14% $BF_3$/methanol reagent. One or two ml of hexane and 1 ml of $BF_3$/methanol reagent are added to lipid samples in glass tubes with Teflon-lined caps. After being flushed with nitrogen, samples are heated at 100° C. for one hour, cooled to room temperature and methyl esters are extracted in the hexane phase following addition of 1 ml $H_2O$. Samples are allowed to stand for 20–30 minutes, the upper hexane layer is removed and concentrated under nitrogen for GC analysis.

Gas chromatography-mass spectrometry. Methylated samples are reconstituted in 100–200 μl hexane or isooctane of which 1–2 μl will be analyzed by gas chromatography. An Omegawas column (30 m; Supelco, Bellefonte, Pa.) will be used in a Hewlett-Packard 5890A gas chromatograph (Hewlett-Packard, Avondage, Pa.). Carrier gas is hydrogen (2.39 ml/min), injected with a split ratio of 1:31. The temperature is initially 165° C. for 5 minutes, then is increased to 195° C. at 2.5° C./min and, from there, to 220° C. at 5° C./min. The temperature is held for 10.5 minutes and then decreased to 165° C. at 27.5° C./min. Peaks will be identified by comparison with fatty acid standards (Nu-Chek-Prep, Elysian, Minn.), and area percentage for all resolved peaks will be analyzed using a Perkin-Elmer M1 integrato (Perkin-Elmer, Norwood, Conn.). These analytical conditions separates all saturated, mono, di- and polyunsaturated fatty acids from C14 to C25 carbons in chain length. The sample size will be calculated based on external standards when added. In addition, the gas chromatography-mass spectrometry (GC-MS) will be carried out using a Hewlett-Packard mass selective detector (model 5972) operating at an ionization voltage of 70 eV with a scan range of 20–500 Da. The mass spectrum of any new peak obtained will be compared with that of standards (Nu Chek Prep, Elysian, Minn.) in the database NBS75K.L (National Bureau of Standards).

Example 7

Evaluation of n-3 desaturase Gene Transfer In Vivo

The experiments described here allow introduction of the fat-1 gene into animal tissues or organs (e.g., heart), where the enzyme product can quickly optimize fatty acid profiles by increasing the content of n-3 PUFAs and decreasing the content of n-6 PUFAs. The heart is selected as an experimental target for the gene transfer because it has been well studied in relation to n-3 fatty acids, and it is a vital organ.

Figure 7:
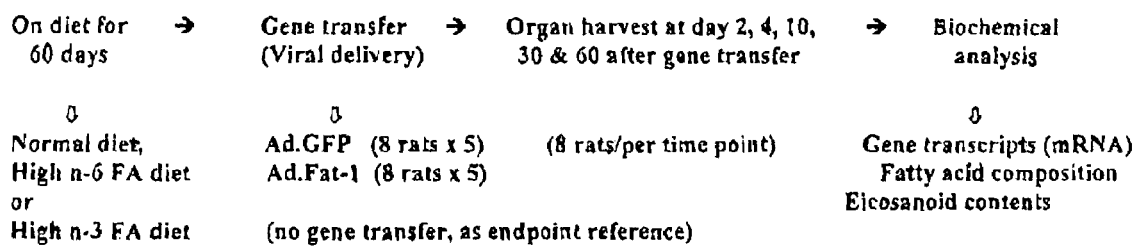
FIG. 7 is a flowchart of an experimental protocol.

Adult rats, fed a normal diet or a diet high in n-6 PUFA for two months, will be randomized to receive either an adenovirus carrying the fat-1 gene (Ad.GFP.fat-1) or an adenovirus carrying the reporter gene GFP (Ad. GFP, as control). The adenoviruses will be delivered to the heart of a living animal using a catheter-based technique, which can produce an expression pattern that is grossly homogeneous throughout the heart (Hajjar et al., *Proc. Natl. Acad. Sci. USA* 95:525105256, 1998). Two days, 4 days, 10 days, 30 days and 60 days after infection (gene transfer), animals will be sacrificed, and their hearts will be harvested and used for determination of the transgene expression and analysis of fatty acid composition. Another group of rats will be fed a diet rich in n-3 fatty acids (low n-6/n-3 ratio) for two months without gene transfer and used as references. These experiments (in which animals are on different diets and samples harvested at different time points) are designed to determine whether transfer of the fat-1 gene can bring about a desired biochemical effect (n-6/n-3 ratio, eicosanoid profile) similar to or even superior to that induced by dietary intervention (i.e., n-3 FA supplementation), how quickly a significant change in fatty acid composition can be achieved, and how long the change can last. Rats injected with the reporter (GFP) gene will be used as controls (our preliminary studies showed that gene transfer of GFP has no effect on fatty acid composition). The experimental flow chart is shown in FIG. 7.

Animals and Diets: weight-matched adult Sprague-Dawley rats will be randomly assigned to three groups. Each group is fed with one of three different diets: normal (basal) diet, a high n-6 diet, or a high n-3 diet. These diets are prepared as follows.

Basal diet: a commercial rat fat-free diet (Agway Inc. C.G., Syracuse, N.Y.) to which 2% (w/w) corn oil is added; High n-6 diet: the basal diet supplemented by addition of a further 13% (w/w) corn oil or safflower oil (high in n-6 fatty acids), bringing the final diet to a total of 15% fat; High n-3 diet: the basal diet supplemented with 13% (w/w) fish oil (30% EPA, 20% DHA, 65% total n-3 PUFA) (Pronova Biocare A/S, Oslo), bringing the final diet to a total of 15% fat. This group will serve as a control group for this study.

The diets will be prepared in small batches weekly, kept at −20° C. and thawed daily in the amounts required. Vitamin E (100 mg/100 g fat) and butylated hydroxy toluene (final concentration 0.05%) will be added to prevent oxidation of long-chain polyunsaturated fatty acids (The BHT should serve to prevent autooxidation of the unsaturated fatty acids during preparation and storage). To ensure animals are receiving adequate nutrition, the rats in all groups will be weighted weekly. After 8 weeks on the diets, the animals will be subjected to gene transfer.

Adenoviral Delivery Protocol. The delivery of adenoviruses to the heart will be performed by using a cathether-based technique similar to that described by Hajjar et al (supra). Briefly, rats will be anesthetized with intra peritoneal pentobarbital (60 mg/kg) and placed on a ventilator. The chest is entered from the left side through the third intercostals space. The pericardium is opened and a 7–0 suture placed at the apex of the left ventricle. The aorta and pulmonary artery are identified. A 22-gauge catheter containing 200 μL adenovirus ($9$–$10 \times 10^{10}$ pfu/ml) is advanced from the apex of the left ventricle (LV) to the aortic root. The aorta and pulmonary arteries are clamped distal to the site of the catheter, and the solution is injected. The clamp is maintained for 10 seconds while the heart pumped against a closed system (isovolumically). After 10 seconds, the clamp on the aorta and pulmonary artery is released, the chest is closed, and the animals are extubated and transferred back to their cages.

At day 2, 4, 10, 30 and 60 after gene transfer, animals will be sacrificed, their hearts infected with the viruses will be removed, perfused or rinsed with saline to removed all blood and a portion of the tissues will be promptly frozen at −80°

C. for lipid analysis and eicosanoid measurement. The remaining tissues will be used for determination of the mRNA levels and/or protein levels of the n-3 desaturase.

It is possible that other organs such as brain and liver may also be infected at high levels by the adenoviruses entering the blood stream. Thus, other organs, in addition to the heart, will be also harvested for analyses of transgene expression and lipid profile.

Other methods, including assessment of transgene expression (by Northern blot, RNase protection assay, or in situ hybridization), analysis of fatty acid composition, measurement of eicosanoids, and statistical analysis will be carried out, as described above in the context of cultured cells.

Example 8

Transgenic Animals

The studies described here are designed to create transgenic mice that globally express the fat-1 gene and to characterize the tissue and organ lipid profiles of these animals. Transgenic mice have become a valuable model for evaluation of physiological significance of a gene in vivo. Availability of transgenic mice allows us to study the effect of a transgene in a variety of cell types at different stages of an animal's lifespan. This n-3 transgenic mouse model will provide new opportunities to elucidate the roles of n-3 PUFA and compounds derived from them in the development and cell biology.

Figure 8:
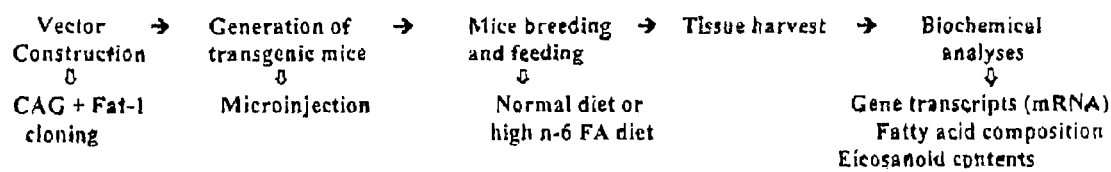
FIG. 8 is a flowchart of an experimental protocol.

To generate transgenic animals that can globally express the fat-1 gene, one can use an expression vector that contains a fat-1 gene and the chicken beta-actin promotor with the CMV enhancer (CAG promotor), which is highly active in a wide range of cell types and therefore allows high-level and broad expression of the transgene (Niwa et al., *Gene* 108:193–199, 1991; Okabe et al., *FEBS Lett.* 407:313–319, 1997). The expression construct will be microinjected into the pronuclei of one-cell embryos of C57BL/6×C3H mice to produce transgenic mice. They will be bred and transgenic mouse line is established. Weanling mice are fed either a normal diet or a diet high in n-6 PUFA. Various tissues will be harvested from these animals at different ages (neonate, wean—1 month, adult—6 ms and aging—12 ms, 3–5 mice per time point will be used) for assessment of the expression levels of the transgene and determination of fatty acid composition. The levels of eicosanoids in plasma and various tissues will also be measured. A group of wild-type mice (C57BL/6) fed with the same diet (either a normal diet or a high n-6 diet) will be used as controls. The results will be compared with those from wild type animals fed the same diet. The procedure is illustrated in FIG. 8.

The transgene will be prepared by methods similar to those described by Okabe et al. (supra). Briefly, a cDNA encoding the fat-1 gene is amplified by PCR with primers, 5-agaattcggcacgagccaa gtttgaggt-3' (SEQ ID NO:1) and 5'-gcctgaggctttatgcattcaacgcact-3' (SEQ ID NO:2), using pCE8-fat1 (provided by Dr. J. Browse, Washington State University) as a template. No additional amino acid sequence is added on either side of the fat-1. The PCR product will be confirmed by DNA sequencing. The EcoR1 and Bgl-II sites included in the PCR primers are used to introduce the amplified fat-1 cDNA into a pCAGGS expression vector containing the chicken beta-actin promoter and cytomegalovirus enhancer, beta-actin intron and bovine globin poly-adenylation signal (provided by Dr. J Miyazaki, Osaka University Medical School). The entire insert with the promoter and coding sequence will be excised with BamHI and SalI and gel-purified.

Transgenic mouse lines will be produced by injecting the purified BamHI and SalI fragment into C57BL/6×C3H fertilized eggs. The DNA-injected eggs are transplanted to pseudo-pregnant mice (B6C3F1) to produce transgenic mice. The founder transgenic mice will be identified by PCR and Southern blot analyses of tail DNA and bred with C57BL/6J mice. Offspring (either heterozygote or homozygote) will be used dependent on the expression levels of the transgene or phenotype.

Weanling transgenic mice will be fed either a normal diet or a diet high in n-6 PUFA (see above). Animals will be sacrificed at different ages (neonate, wean to 1 month, adult to 6 mos and aging—12 mos, 3–5 mice per time point will be used) and various tissues will be harvested for assessment of the expression level of transgene and determination of fatty acid composition. The results will be compared with those from wild type animals fed the same diet.

Other methods, including assessment of transgene expression (Northern blot, RNase protection assays, or in situ hybridization), analysis of fatty acid composition, measurement of eicosanoids, and statistical analyses will be carried out as described above.

Example 9

Inhibition of Neuronal Cell Death

Construction of Recombinant Adenovirus (Ad): A recombinant Ad carying the fat-1 gene was constructed as described previously (Kang et al., *Proc. Natl. Acad. Sci. USA* 98;4050–4054, 2001; see also, above). The n-3 fatty acid desaturase cDNA (fat-1 gene) used was that described above, provided in plasmid pCE8. The fat-1 cDNA was excised from the plasmid with an EcoRI/KpnI digestion, and inserted into pAdTrack-CMV vector. The construct was subsequently recombined homologously with an adenoviral backbone vector (pAdEasy 1) to generate two clones: Ad-GFP, which expresses GFP as a reporter or marker, and Ad-GFP-fat-1, which carries both the fat-1 and the GFP genes, each under the control of separate CMV promoters. Recombinant adenoviral vector DNA was digested with PacI. The linerized vector DNA was mixed with SuperFect™ (QIAGEN) and used to infect 293 cells. The recombinant viruses were prepared as high-titer stocks through propagation in 293 cells. The integrity of the constructs was confirmed by enzymatic digestion (i.e., restriction mapping) and by DNA sequencing. Purified virus was checked and its sequence confirmed again by PCR analysis.

Tissue Culture and Infection with Ad: Rat cortical neurons were prepared using standard techniques. Briefly, prenatal embryonic day 17 (E17) rat cortical neurons were dissociated and plated in poly-lysine-coated wells at $2 \times 10^6$ cells/well. The cells were grown in Neurobasal™ Medium (NBM, Life Technologies) supplemented with 25 μM glutamic acid (Sigma Chemical Co., St. Louis, Mo.), 0.5 mM glutamine, 1% antibiotic-antimycotic solution, and 2% B27 (Life Technologies). Cultures were kept at 37° C. in air with 5% $CO_2$ and 98% relative humidity. The culture medium was changed every four days. After 8–10 days in culture, cells were transfected with either the Ad-GFP (control) or the Ad-GFP-fat-1 plasmids. Viral infections were carried out by adding viral particles to the culture medium. After a 48-hour incubation, cells were used for analyses of gene expression, fatty acid composition, eicosanoid production, and induction of apoptosis.

RNA Analysis: The level of fat-1 expression was determined by probing for mRNA transcripts in an RNAse protection assay using the RPA III™ kit (Ambion, Austin, Tex.). Briefly, total RNA was extracted from cultured cells using a total RNA isolation reagent (TRizol, GIBco BRL) according to the manufacturer's protocol. The plasmid containing the fat-1 gene, pCE8, was linearized and used as a transcription template. Antisense RNA probes were transcribed in vitro using [$^{33}$P]-UTP, T7 polymerase (Riboprobe System™ T7 kit, Promega), hybridized with total RNA (15 μg) extracted from neurons, and digested with ribonuclease to remove nonhybridized RNA and probe. The protected RNA-RNA hybrids were resolved in a denaturing 5% sequence gel and subjected to autoradiography. A probe targeting the β-actin gene was used as an internal control. fat-1 mRNA was not detected in cells infected with Ad-GFP (control), but was highly abundant in cells infected with Ad-GFP-fat-1.

The cells were also examined by fluoresence microscopy. Infected cells that expressed the fat-1 gene were readily identifiable because they co-expressed GFP. Forty-eight hours after infection, 30–40% of the neurons were infected and expressed GFP. These results demonstrate that Ad-mediated gene transfer confers high expression of fat-1 gene in rat cortical neurons, which normally lack the gene.

Lipid Analysis: The fatty acid composition of total cellular lipids was analyzed as described in Kang et al. (*Proc. Natl. Acad. Sci. USA* 98:4050–4054, 2001). Lipid was extracted with chloroform:methanol (2:1, vol:vol) containing 0.005% butylated hydroxytoluene (BHT, as an antioxidant). Fatty acid methyl esters were prepared using a 14% (wt/vol) BF3/methanol reagent. Fatty acid methyl esters were quantified with GC/MS by using an HP-5890 Series II gas chromatograph equipped with a Supelcowax™ SP-10 capillary column (Supelco, Bellefonte, Pa.) attached to an HP-5971 mass spectrometer. The injector and detector are maintained at 260° C. and 280° C., respectively. The oven program is maintained initially at 150° C. for 2 minutes, then ramped to 200° C. at 10° C./minute and held for 4 minutes, ramped again at 5° C./minute to 240° C., held for 3 minutes, and finally ramped to 270° C. at 10° C./minute and maintained for 5 minutes. Carrier gas-flow rate is maintained at a constant 0.8 ml/min throughout. Total ion monitoring is performed, encompassing mass ranges from 50–550 atomic mass units. Fatty acid mass is determined by comparing areas of various analyzed fatty acids to that of a fixed concentration of internal standard.

The expression of fat-1 resulted in conversion of n-6 fatty acids to n-3 fatty acids, and thus a significant change in the ratio of n-6:n-3 fatty acids. The fatty acid profile obtained from control cells is significantly different from that of cells infected with Ad-GFP-fat-1 (FIG. 9; see also FIG. 10). Cells infected with Ad-GFP show no change in fatty acid composition when compared with non-infected cells. In cells expressing the n-3 desaturase, almost all types of n-6 fatty acids were converted to the corresponding n-3 fatty acids, namely, 18:2n-6 to 18:3n-3, 20:4n-6 to 20:5n-3, 22:4n-6 to 22:5n-3, an 22:5n-6 to 22:6n-3. The change in fatty acid composition of the cells expressing the fat-1 gene resulted in reduction of the n-6:n-3 ratio from 6.4:1 in the control cells to 1.7:1 in the cells expressing the n-3 desaturase. Expression of the *C. elegans* n-3 fatty acid desaturase resulted in a significant increase in the levels of DHA in transfected cells. An increase in levels of EPA and ALA is observed with a concomitant decrease in AA and LA suggesting that the decrease in production of $PGE_2$ resulted from both the shift in the n-6:n-3 fatty acid ratio and from DHA-mediated inhibition of AA hydrolysis.

Figure 11:
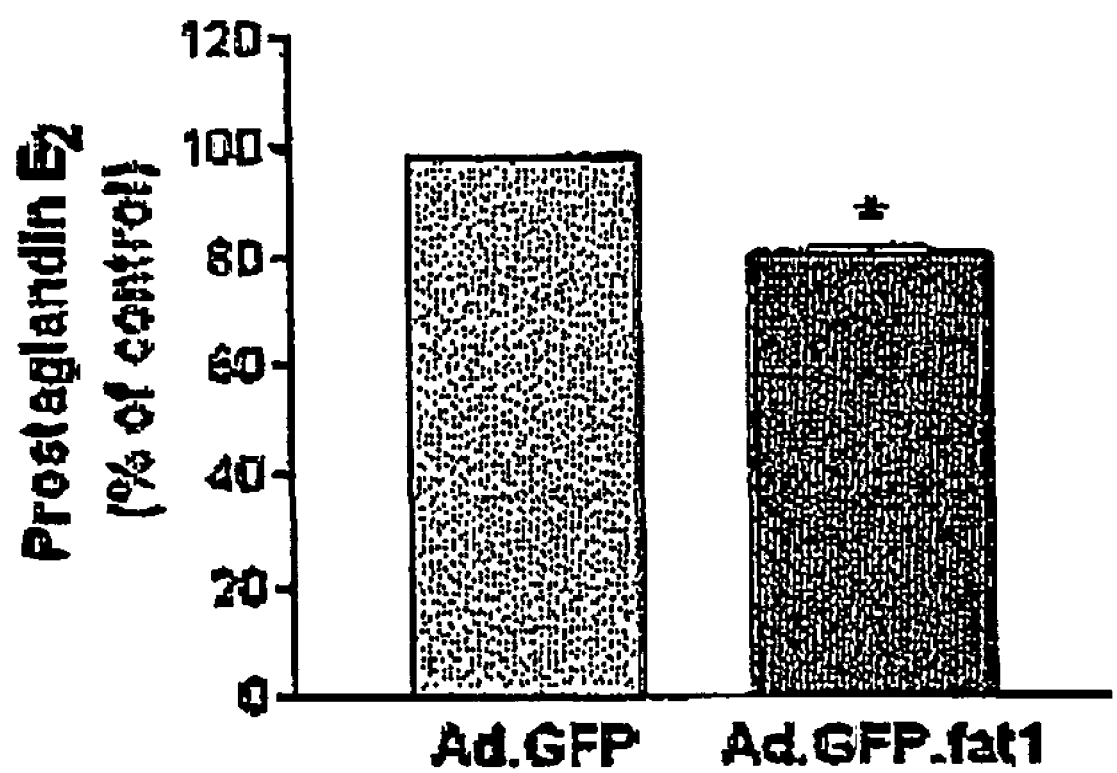
FIG. 11 is a bar graph showing the results of an enzyme immunoassay of prostaglandin $E_2$ levels in control neurons and neurons expressing the fat-1 gene. Ad-GFP-fat-1 infected neurons have lower levels of $PGE_2$ relative to control. Values are means±SD of three experiments and expressed as a percentage of control. *P<0.01.

Measurement of Eicosanoids: 2-series eicosanoids may be associated with neuronal apoptosis in age-associated neurodegenerative diseases and acute excitotoxic insults such as ischemia (Sanzgiri et al., *J. Neurobiol.* 41:221–229, 1999; Drachman and Rothstein, *Ann. Neurol.* 48:792–795, 2000; Bezzi et al., *Nature* 391:281–285, 1998). Arachidonic acid (AA, 20:4n-6) and eicosapentaenoic acid (EPA, 20:5n-3) are the precursors of 2- and 3-series of eicosanoids, respectively. To determine whether the gene transfer-mediated alteration in the contents of AA and EPA may lead to a difference in the production of eicosanoids in the cells, we measured the production of prostaglandin $E_2$, one of the major eicosanoids derived from AA, in infected cells after stimulation with calcium ionophore A23187. More specifically, prostaglandin $E_2$ was measured by using enzyme immunoassay kits (Cayman Chemical, Ann Arbor, Mich.) following the manufacturer's protocol. (The crossreactivity with prostaglandin E3 is 16%.) Cultured cells were washed with LH buffer (with 1% BSA) and incubated with the same buffer containing the calcium ionophore A23187 (5 μM). After a 10-minute incubation, the conditioned buffer was recovered and subjected to eicosanoid measurement. The amount of prostaglandin $E_2$ produced by fat-1 expressing cells was 20% lower than that produced by control cells (FIG. 11).

Induction of apoptosis and determination of cell growth and viability: Apoptosis was induced by growth factor withdrawal. Forty-eight hours after neurons were transfected, the culture media was changed to Neurobasal™ Medium supplemented with 25 mM glutamic acid (Sigma Chemical Co., St. Louis, Mo.) and 0.5 mM glutainine. Cytotoxicity was measured 24 hours after growth factors were withdrawn using the Vybrant™ Apoptosis Assay (Molecular Probes, Eugene, Oreg.). Briefly, cells were washed with ice-cold phosphate buffered saline (PBS) and subsequently incubated on ice for 20–30 min in ice-cold PBS containing Hoechst 33342 solution (1 ml/ml) and PI solution (1 ml/ml). A photograph was taken at the end of the incubation period.

Cell growth and viability: Cell growth and viability were determined using the MTT cell proliferation kit (Roche Diagnostic Corporation). MTT labeling reagent (100 μl) was added to each well. After 4 hours of incubation, 1.0 ml of the solubilization solution was added into each well. The cells were then incubated overnight at 37° C. and the spectrophotometrical absorbency of the solution at 600 nm was measured.

Figure 12:
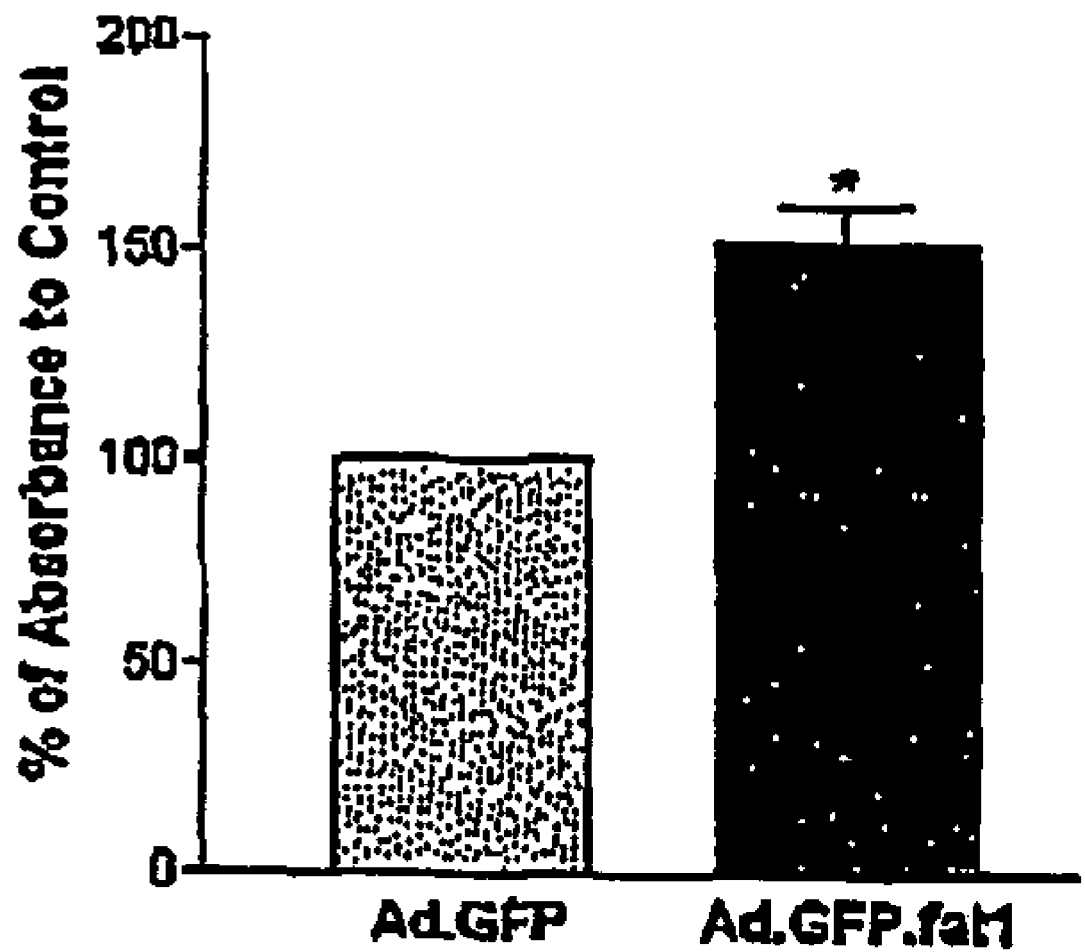
FIG. 12 is a bar graph representing the results of an MTT assay of cell viability in control and fat-1 expressing cultures. After 24 hours of growth factor withdrawal, the cell viability of neurons expressing the fat-1 gene is 50% higher than control cells (p<0.01).

Expression of the fat-1 gene provided strong protection against apoptosis in rat cortical neurons. Hoest 33625 and PI staining of cortical cultures 24 hours after the induction of apoptosis, show that cultures infected with Ad-GFP-fat-1 underwent less apoptosis than those infected with Ad-GFP. MTT analysis indicated that the viability of Ad-GFP-fat-1 cells was significantly (p<0.05) higher than that of cells infected with Ad-GFP (FIG. 12). These results indicate that the expression of fat-1 can inhibit neuronal apoptosis and promote cell viability. The ability of the *C. elegans* n-3 fatty acid desaturase to inhibit apoptosis of neuronal cells highlights the importance of the n-6:n-3 fatty acid ratio in neuroprotection. Accordingly, techniques that deliver a fat-1 sequence, or a biologically active variant thereof, to neurons provide the means to quickly and dramatically balance cellular n-6:n-3 fatty acid ratio, alter eicosanoid profile (and thereby exert an anti-apoptotic effect on neuronal cells) without the need for supplementation with exogenous n-3 PUFAs. Compared to dietary intervention, this approach is more effective in balancing the n-6:n-3 ratio because it simultaneously elevates the tissue concentration of n-3 PUFAs and reduces the level of endogenous n-6 PUFAs. This method is a novel and effective approach to modifying fatty acid composition in neuronal cells, and it can be applied as a stand-alone gene therapy or as an adjuvant therapy or chemopreventive procedure (in, for example, apoplexy patients).

Data analysis, statistical analysis: Cell viability data (MTT), as well as fatty acid composition and eicosanoids levels were compared using the Student t-test. The analysis included 6 wells/group (except lipid analyses; 4 wells/group) and each experiment was repeated 3 times. The level of significance was set at p<0.05.

Example 10

Fat-1 Expression in Human Endothelium and Inhibition of Inflammation

To determine whether the conversion of n-6 to n-3 PUFA can be genetically conferred to primary human vascular endothelium and to study its potential protective effects against endothelial activation after cytokine stimulation, a first generation (type 5) recombinant adenoviral vector (Ad) was constructed which contained the fat-1 transgene in series with a GFP expression cassette under the control of the CMV promoter (Ad.fat-1). A GFP/β-gal adenovirus served as the control vector (Ad.GFP/β-gal). Monolayers of primary human umbilical vein endothelial cells (HUVECs) were infected with Ad.fat-1 or the control Ad for 36 hours, exposed for 24 hours to 10 mM arachidonic acid, and subjected to lipid analysis by gas chromatography, surface adhesion molecule analysis by inimunoassay, and videomicroscopy to study endothelial interactions with the monocytic cell line, THP-1, under laminar flow conditions.

Expression of fat-1 dramatically altered the lipid composition of human endothelial cells and changed the overall ratio of n-6 to n-3 PUFA from 8.5 to 1.4. Furthermore, after cytoline exposure (TNF-α, 5 μl applied for 4 hours) fat-1 expression significantly reduced the surface expression of the adhesion molecules and markers of inflammation (E-Selectin, ICAM-1, and VCAM-1 by 42%, 43%, and 57%, respectively (p<0.001)).

We then asked whether changes in the adhesion molecule profile were sufficient to alter endothelial interactions with monocytes, the most prevalent white blood cell type found in atherosclerotic lesions. Under laminar flow and a defined shear stress of ~2 dynes/cm$^2$, fat-1-infected HUVEC, compared to control vector-infected HUVEC, supported ~50% less firm adhesion with almost no effect on the rolling interactions of THP-1 cells. Thus, heterologous expression of the *C. elegans* desaturase, fat-1, confers on human endothelial cells the ability to convert n-6 to n-3 PUFA. This effect significantly repressed cytokine induction of the endothelial inflammatory response and firm adhesion of the monocytic cell line, THP-1, under simulated physiological flow conditions. Accordingly, expression of fat-1 represents a potential therapeutic approach to treating inflammatory vascular diseases, such as atherosclerosis.

Example 11 n-3 Desaturase as an Anti-Arrhythmic Agent

To determine whether fat-1 expression could provide an anti-arrhythmic effect, myocytes expressing the n-3 desaturase were examined for their susceptibility to arrhythmias induced by arrhythmogenic agents. Neonatal rat cardiac myocytes, grown on glass coverslips and able to spontaneously beat, were infected with Ad.GFP.fat-1 or Ad.GFP. Two days after infection, cells were transferred to a perfusion system and perfused with serum free medium containing high concentrations (5–10 mM) of calcium. These media are arrhythmogenic. During the perfusion process, myocyte contraction was monitored using a phase contrast microscope and video-monitor edge-detector. Following the high [Ca$^{2+}$] (7.5 mM) challenge, the control cells infected with Ad.GFP promptly exhibited an increased beating rate followed by spasmodic contractions or fibrillation whereas the cells infected with Ad.GFP.fat-1 could sustain regular beating. Thus, myocytes expressing the n-3 desaturase show little, if any, susceptibility to arrhythmogenic stimuli (FIG. 13).

Example 12

Fat-1 Expression and Inhibition of Tumor Growth

Figure 14:
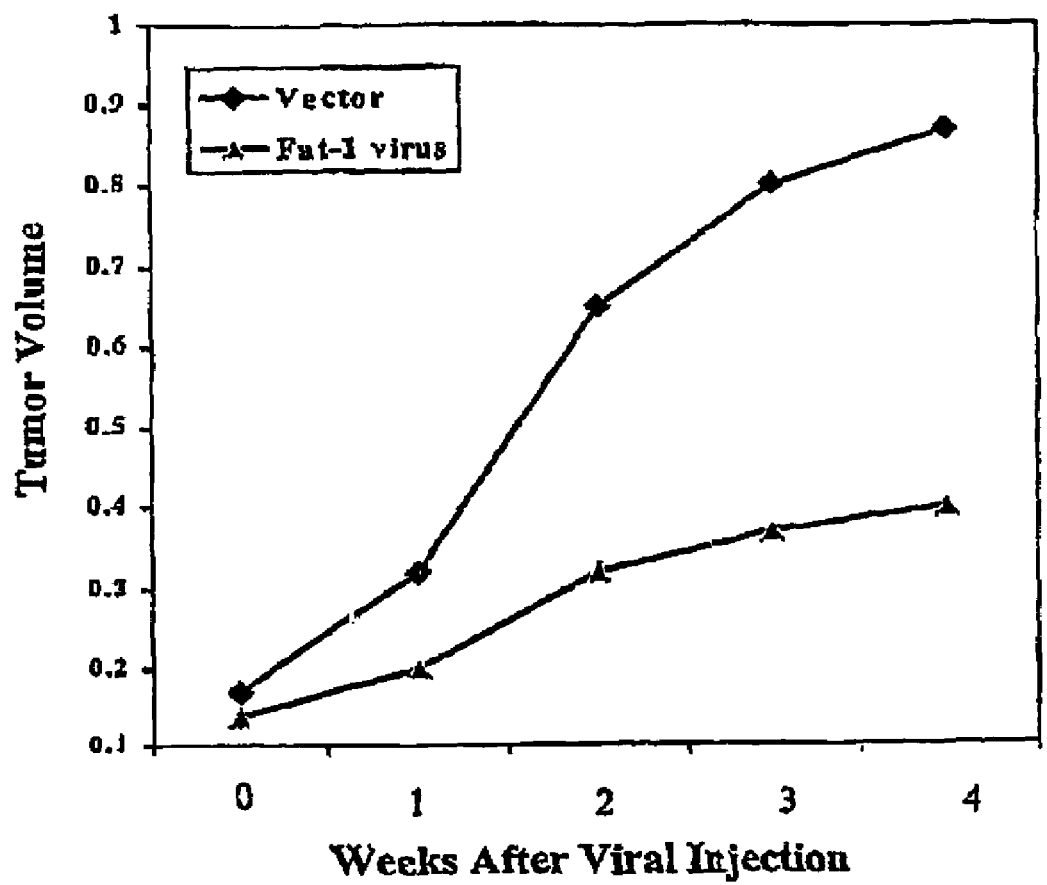
FIG. 14 is a line graph showing tumor volume over time (0–4 weeks after viral injection) and thus, the effect of gene transfer on tumor growth. Breast cancer cells (MDA-MB-231) were implanted subcutaneously on the back of nude mice. Three weeks later, the mice were treated with Ad.GFP-fat-1 or Ad.GFP (control; 50 µl, $10^{12}$ VP/m) by intratumoral injection.

To test the effect of the gene transfer on tumor growth in vivo, we have carried out a pilot experiment in two nude mice bearing human breast cancer xenografts (MDA-MB-231). One mouse was injected intratumorally with 50 ml of Ad.GFP.fat-1 (1012 particles/ml) twice every other day. The other was injected with the control vector (Ad.GFP). The growth rate of the tumors was monitored for four weeks. The growth rate of the tumor treated with Ad.GFP.fat-1 appeared to be slower than that of the control tumor (FIG. 14).

Example 13

The Effect of Fat-1 Expression on Fatty Acid Composition and Growth of Human Breast Cancer Cells in Culture Construction of Recombinant Adenovirus (Ad): A recombinant Ad carrying the fat-1 cDNA was constructed as described previously (Kang et al., *Proc. Natl. Acad. Sci. USA* 98:4050–4054, 2001). Briefly, the fat-1 cDNA in pCE8 (as described above) was excised from the plasmid with an EcoRI/KpnI double digest, inserted into a shutter vector and then subjected to homologous recombination with an adenoviral backbone according to the methods of He et al. (*Proc. Natl. Acad. Sci. USA* 95:2509–2514, 1998). Two first-generation type 5 recombinant adenoviruses were generated: Ad.GFP, which carries GFP as a reporter gene under control of the CMV promoter, and Ad.GFP.fat-1, which carries both the fat-1 and GFP genes, each under the control of separate CMV promoters. The recombinant viruses were prepared as high titer stocks through propagation in 293 cells, as described previously (Kang et al., *Proc. Natl. Acad. Sci. USA* 98:4050–4054, 2001). The integrity of the constructs was confirmed by enzymatic digestion and by DNA sequence analysis.

Cell Cultures and Infection with Ad.: MCF-7 cells were routinely maintained in 1:1 (v/v) mixture of DMEM and Ham's F12 medium (JRH, Bioscience) supplemented with 5% fetal bovine serum (FBS) plus antibiotic solution (penicillin, 50 U/ml; streptomycin, 50 µg/ml) at 37° C. in a tissue culture incubator with 5% $CO_2$ and 98% relative humidity. Cells were infected with Ad for experiments when they were grown to about 70% confluence by adding virus particles to medium without serum ($3-5\times10^8$ particles/ml). Initially, optimal viral concentration was determined by using Ad.GFP to achieve an optimal balance of high gene expression and low viral titer to minimize cytotoxicity. After a 24-hour incubation, the infection medium was replaced with normal culture medium supplemented with 10 µM 18:2n6 and 20:4n6. Forty-eight hours after infection, cells were used for analyses of gene expression, fatty acid composition, eicosanoid production, and cell proliferation and apoptosis.

RNA Analysis: The fat-1 transcripts were examined by ribonuclease protection assay using a RPA III™ kit (Ambion, Austin, Tex.). Briefly, total RNA was extracted from cultured cells using a RNA isolation kit (Qiagen) according to the manufacturer's protocol. The plasmid containing fat-1, pCE8, was linearized and used as transcription template. Antisense RNA probes were transcribed in vitro using $^{33}$P-UTP and T7 polymerase (Riboprobe™ System T7 kit, Promega), hybridized with the total RNA extracted from the cancer cells, and digested with RNase to remove non-hybridized RNA and probe. The protected RNA:RNA was resolved in denaturing sequence gel and subjected to autoradiography. A probe targeting the GAPDH gene was used as an internal control.

The cells that were infected and expressed the transgene could be readily identified by fluorescence microscopy since they co-expressed the GFP (which exhibites bright fluorescence). Three days after infection, it was observed that about 60–70 percent of the cells were infected and expressed the transgene. Analysis of mRNA using a ribonuclease protection assay showed that fat-1 mRNA was highly abundant in cells infected with Ad.GFP.fat-1, but was not detected in cells infected with Ad.GFP (control). This result indicates that the Ad-mediated gene transfer could confer a high expression of fat-1 gene in MCF-7 cells, which normally lack the gene.

Lipid Analysis: To examine the efficacy of the gene transfer in modifying the fatty acid composition of the human MCF-7 cells, total cellular lipids were extracted and analyzed by gas chromatograph after infection with the Ads and incubation with n-6 fatty acids for 2–3 days. The fatty acid composition of total cellular lipids was analyzed as described (Kang et al., supra). Lipid was extracted with chloroform/methanol (2:1, vol/vol) containing 0.005% butylated hydroxytoluene (BHT, as antioxidant). Fatty acid methyl esters were prepared by using a 14% (wt/vol) BF3/methanol reagent. Fatty acid methyl esters were quantified with GC/MS by using an HP-5890 Series II gas chromatograph equipped with a Supelcowax SP-10 capillary column (Supelco, Bellefonte, Pa.) attached to an HP-5971 mass spectrometer. The injector and detector are maintained at 260° C. and 280° C., respectively. The oven program is maintained initially at 150° C. for 2 min, then ramped to 200° C. at 10° C./min and held for 4 min, ramped again at 5° C./min to 240° C., held for 3 min, and finally ramped to 270° C. at 10° C./min and maintained for 5 min. Carrier gas-flow rate is maintained at a constant 0.8 ml/min throughout. Total ion monitoring is performed, encompassing mass ranges from 50–550 atomic mass units. Fatty acid mass is determined by comparing areas of various analyzed fatty acids to that of a fixed concentration of internal standard.

The expression of fat-1 cDNA in MCF-7 cells resulted in conversions of n-6 fatty acids to n-3 fatty acids, and a significant change in the ratio of n-6/n-3 fatty acids. The fatty acid profiles are remarkably different between the control cells infected just with the Ad.GFP and the cells infected with the Ad.GFP.fat-1 (FIG. 15). Cells infected with Ad.GFP had no change in their fatty acid profiles when compared with noninfected cells. In the cells expressing the fat-1 cDNA (n-3 fatty acid desaturase), various n-6 fatty acids were converted largely to the corresponding n3 fatty acids, for example, 18:2n6 to 18:3n3, 20:4n6 to 20:5n3, and 22:4n6 to 22:5n3. As a result, the fatty acid composition of the cells expressing fat-1 gene was changed significantly when compared with that of the control cells infected with Ad.GFP (FIG. 15), with a large reduction of the n-6/n-3 ratio from 12 in the control cells to 0.8 in the cells expressing the n-3 fatty acid desaturase.

Figure 16:
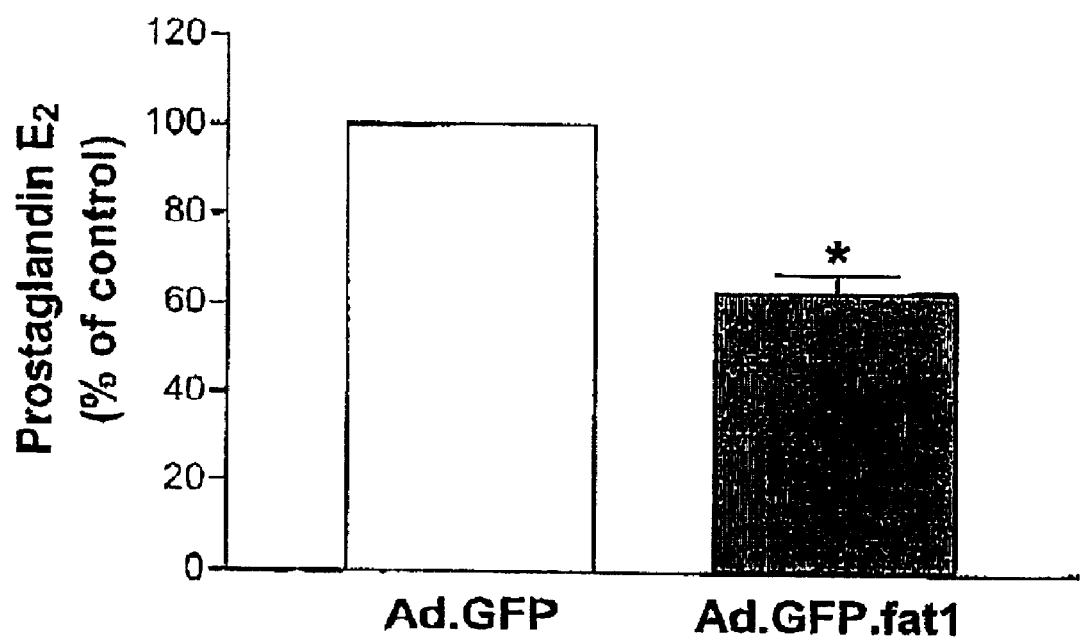
FIG. 16 is a bar graph depicting the results of an enzyme immunoassay of prostaglandin $E_2$ levels in control MCF-7 cells and MCF-7 cells expressing fat-1 gene. Values are means±SE of three experiments and expressed as a percentage of control. (*P<0.05).

Measurement of Eicosanoids: It has been shown previously that prostaglandin E2 (PGE2), one of the major ecosanoids derived from 20:4n6 (arachidonic acid), is associated with cancer development (Rose and connolly, Pharmacol. ther. 83:217–244, 1999; cave, Breast Cancer Res. Treat. 46:239–246, 1997). To determine whether the gene transfer-induced alteration in the contents of arachidonic and eicosapentaenoic acids can change the production of eicosanoids in the cells, we measured the production of PGE2 in the infected cells after stimulation with calcium ionophore A23187 by using an enzyme immunoassay kit that specifically detects prostaglandin E2 derived from AA with a 16% crossreactivity with prostaglandin E3 from EPA. More specifically, prostaglandin $E_2$ was measured by using enzyme immunoassay kits (Assay Designs, Inc) following the manufacturer's protocol. (The cross-reactivity with $PGE_3$ is 16%). Cultured cells were washed with PBS containing 1% BSA and incubated with serum-free medium containing calcium ionophore A23187 (5 µM). After a 10-minute incubation, the conditioned medium was recovered and subjected to eicosanoid measurement. The amount of prostaglandin $E_2$ produced by the fat-1 cells was significantly lower than that produced by the control cells (FIG. 16).

Analysis of Cell Proliferation and Apoptosis: To determine the effect of expression of the fat-1 gene on MCF-7 cell growth, cell proliferation and apoptosis following gene transfer were assessed. Routinely, cell morphology was examined by microscopy (dead cells appear to be detached, round and small) and total number of cell in each well was determined by counting the viable cells using a hemocytometer. In addition, cell proliferation was assessed using a MTT Proliferation Kit I (Roche Diagnostics Corporation). Apoptotic cells were determined by nuclear staining with Vybrant™ Apoptosis Kit #5 (Molecular Probes) following the manufacturer's protocol.

A large number of the cells expressing fat-I gene underwent apoptosis, as indicated by morphological changes (small size with round shape or fragmentation) and nuclear staining (bright blue). Statistic analysis of apoptotic cell counts showed that 30–50% of cells infected with Ad.GFP.fat-1 were apoptotic whereas only 10% dead cells found in the control cells (infected with Ad.GFP). MTT analysis indicated that proliferative activity of cells infected with Ad.GFP.fat-1 was significantly lower than that of cells infected with Ad.GFP. Accordingly, the total number of viable cells in the cells infected with Ad.GFP.fat-1 was about 30% less than that in the control cells. These results are consistent with the proposition that fat-1 expression can serve as an anti-cancer agent.

Data analyses, statistical analyses: Data were presented as mean ±SE. Student's T test was used to evaluate the difference between two values. The level of significance was set at $p<0.05$.Results A number of embodiments of the invention have been described. Nevertheless, it will be understood that various modifications may be made without departing from the spirit and scope of the invention.

What is claimed is:

1. A nonhuman transgenic mammal whose genome comprises a nucleic acid molecule comprising a nucleotide sequence operably linked to a promoter, wherein the nucleotide sequence encodes the amino acid sequence of SEQ ID NO:4 or an amino acid sequence that is (i) a biologically active variant of SEQ ID NO:4 and (ii) at least 90% identical to SEQ ID NO:4, and upon expression of the nucleotide sequence in cells within the transgenic mammal, the n-3 polyunsaturated fatty acid (PUFA) content is elevated compared to that of cells of a wild-type mammal, wherein the transgenic mammal is selected from the group consisting of a mouse, a cow, a pig, a sheep, a goat, and a rabbit.

2. The transgenic mammal of claim 1, wherein the amino acid sequence is at least 95% identical to SEQ ID NO:4.

3. The transgenic mammal of claim 1, wherein the amino acid sequence is at least 99% identical to SEQ ID NO:4.

4. The transgenic mammal of claim 1, wherein the nucleotide sequence encodes SEQ ID NO:4.

5. The transgenic mammal of claim 1, wherein the nucleotide sequence comprises SEQ ID NO:3.

6. The transgenic mammal of claim 1, wherein the nucleotide sequence consists of SEQ ID NO:3.

7. The transgenic mammal of claim 1, wherein the mammal is a cow.

8. The transgenic mammal of claim 1, wherein the mammal is a pig.

9. The transgenic mammal of claim 1, wherein the mammal is a sheep.

10. The transgenic mammal of claim 1, wherein the mammal is a goat.

11. The transgenic mammal of claim 1, wherein the mammal is a rabbit.

12. The transgenic mammal of claim 1, wherein the biologically active variant is at least 90% as efficient as SEQ ID NO:4 in converting n-6 to n-3 PUFA.

13. The transgenic mammal of claim 1, wherein the biologically active variant is at least 95% as efficient as SEQ ID NO:4 in converting n-6 to n-3 PUFA.

14. The transgenic mammal of claim 1, wherein the biologically active variant is at least 99% as efficient as SEQ ID NO:4 in converting n-6 to n-3 PUFA.

15. A nonhuman transgenic mammal whose genome comprises a nucleic acid molecule comprising a nucleotide sequence operably linked to a promoter, wherein the nucleotide sequence encodes an amino acid sequence that is (i) at least 90% as efficient as SEQ ID NO:4 in converting n-6 to n-3 PUFA and (ii) at least 90% identical to SEQ ID NO:4, and upon expression of the nucleotide sequence in cells within the transgenic mammal the n-3 PUFA content is elevated compared to that of cells of a wild-type mammal, wherein the transgenic mammal is selected from the group consisting of a mouse, a cow, a pig, a sheep, a goat, and a rabbit.

16. A transgenic mouse whose genome comprises a nucleic acid molecule comprising a nucleotide sequence encoding the amino acid sequence of SEQ ID NO: 4 operably linked to a promoter, wherein the mouse exhibits an elevated n-3 PUFA content as compared to a wild-type mouse.

* * * * *